(12) United States Patent
Kuwata et al.

(10) Patent No.: US 7,514,520 B2
(45) Date of Patent: *Apr. 7, 2009

(54) PROCESS FOR PRODUCING PHOSPHONITRILIC ACID ESTER

(75) Inventors: Kotaro Kuwata, Kurashiki (JP); Hiroji Oda, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 335 days.

This patent is subject to a terminal disclaimer.

(21) Appl. No.: 10/557,722

(22) PCT Filed: Jun. 3, 2004

(86) PCT No.: PCT/JP2004/007708

§ 371 (c)(1),
(2), (4) Date: Nov. 21, 2005

(87) PCT Pub. No.: WO2004/108737

PCT Pub. Date: Dec. 16, 2004

(65) Prior Publication Data

US 2007/0060739 A1 Mar. 15, 2007

(30) Foreign Application Priority Data

Jun. 5, 2003 (JP) ............................. 2003-160916

(51) Int. Cl.
*C08G 79/02* (2006.01)
(52) U.S. Cl. .................... 528/167; 528/399; 528/400
(58) Field of Classification Search .............. 528/127, 528/399, 400
See application file for complete search history.

(56) References Cited

U.S. PATENT DOCUMENTS

| | | | | |
|---|---|---|---|---|
| 2,586,312 A * | 2/1952 | Goldschmidt et al. | ....... | 528/399 |
| 3,164,556 A * | 1/1965 | Apley et al. | .................. | 528/381 |
| 3,169,933 A * | 2/1965 | Chui et al. | .................. | 528/395 |
| 3,313,774 A * | 4/1967 | Rice et al. | .................... | 528/168 |
| 3,367,750 A * | 2/1968 | Jaszka et al. | ............... | 423/300 |
| 3,419,504 A * | 12/1968 | Klender | ........................ | 528/399 |
| 3,474,044 A * | 10/1969 | Goldwhite et al. | ........... | 528/398 |
| 3,524,907 A * | 8/1970 | Depaolo et al. | ............... | 558/93 |
| 3,794,701 A | 2/1974 | Bik | | |
| 3,844,983 A * | 10/1974 | Reynard et al. | ............ | 528/399 |
| 3,888,800 A * | 6/1975 | Allcock | ........................ | 528/399 |
| 3,896,058 A * | 7/1975 | Reynard et al. | ............. | 528/399 |
| 3,939,228 A | 2/1976 | Kao | | |
| 3,945,966 A * | 3/1976 | Vicic et al. | ................. | 428/66.4 |
| 3,970,533 A * | 7/1976 | Kyker et al. | ................. | 524/783 |
| 4,071,583 A * | 1/1978 | Hechenbleikner | ............ | 558/77 |
| 4,107,108 A | 8/1978 | Dieck et al. | | |
| 4,116,891 A * | 9/1978 | Dieck et al. | .................... | 521/89 |
| 4,123,503 A * | 10/1978 | Snyder et al. | ............... | 423/300 |
| 4,129,529 A * | 12/1978 | Fieldhouse et al. | .......... | 528/168 |
| 4,223,103 A * | 9/1980 | Schulz et al. | ............... | 528/168 |
| 4,226,972 A * | 10/1980 | Schulz et al. | ............... | 528/168 |
| 4,258,172 A * | 3/1981 | Allcock et al. | .............. | 528/168 |
| 4,258,173 A * | 3/1981 | Schulz et al. | ................ | 528/168 |
| 4,276,403 A * | 6/1981 | Frosch et al. | ................... | 528/4 |
| 4,311,736 A * | 1/1982 | Leong | ......................... | 427/331 |
| 4,357,458 A * | 11/1982 | Antkowiak et al. | .......... | 528/167 |
| 4,382,914 A | 5/1983 | Horie et al. | | |
| 4,446,295 A * | 5/1984 | Shibuta et al. | .............. | 528/168 |
| 4,514,550 A * | 4/1985 | Penton | ....................... | 525/538 |
| 4,523,009 A * | 6/1985 | Neilson et al. | ............... | 528/399 |
| 4,535,095 A * | 8/1985 | Mueller | ........................ | 521/89 |
| 4,600,791 A * | 7/1986 | Carr et al. | ..................... | 558/80 |
| 4,657,993 A * | 4/1987 | Lora et al. | ................... | 525/538 |
| 4,806,322 A * | 2/1989 | Hergenrother et al. | ....... | 423/300 |
| 4,816,532 A * | 3/1989 | Chang | ......................... | 525/538 |
| 4,880,905 A * | 11/1989 | Ueyama et al. | .............. | 528/399 |
| 4,933,479 A * | 6/1990 | Kotaka et al. | ................ | 558/199 |
| 4,946,938 A * | 8/1990 | Magill et al. | ................. | 528/399 |
| 4,959,442 A * | 9/1990 | Ohkawa et al. | .............. | 528/168 |
| 4,988,791 A * | 1/1991 | Maruyama et al. | ........... | 528/168 |
| 5,023,278 A * | 6/1991 | Fisher et al. | ................... | 521/85 |
| 5,041,524 A * | 8/1991 | Gleria et al. | ................. | 528/220 |
| 5,098,574 A * | 3/1992 | Chambrette et al. | ......... | 210/651 |
| 5,101,002 A * | 3/1992 | Klobucar et al. | ............. | 528/168 |
| 5,102,963 A * | 4/1992 | Kolich et al. | ................ | 525/538 |
| 5,104,947 A * | 4/1992 | Schacht et al. | .............. | 525/538 |
| 5,138,008 A * | 8/1992 | Montague et al. | ............. | 528/21 |
| 5,250,626 A * | 10/1993 | Landry et al. | ................ | 525/188 |
| 5,260,103 A * | 11/1993 | Gleria et al. | ................. | 427/520 |
| 5,268,287 A * | 12/1993 | Matsuki et al. | .............. | 435/181 |
| H1309 H * | 5/1994 | Allen et al. | .................. | 442/103 |
| 5,424,385 A * | 6/1995 | Hager et al. | ................. | 528/28 |
| 5,464,932 A * | 11/1995 | Allcock et al. | .............. | 528/399 |
| 5,688,888 A * | 11/1997 | Burkus et al. | ................ | 528/22 |
| 5,716,589 A * | 2/1998 | Kosky et al. | ................ | 423/300 |

(Continued)

FOREIGN PATENT DOCUMENTS

DE 27 54 245 6/1978

(Continued)

*Primary Examiner*—Mark Eashoo
*Assistant Examiner*—Liam J Heincer
(74) *Attorney, Agent, or Firm*—Staas & Halsey LLP

(57) ABSTRACT

A process for producing a phosphonitrilic acid ester. The process comprises using a specific compound as a catalyst to react phosphonitrile dichloride with at least one member selected among phenol compounds and/or alcohol compounds in the presence of a reaction solvent. Alternatively, the process comprises reacting a liquid reaction mixture obtained in a first stage with at least one member selected among phenol compounds and/or alcohol compounds without isolating phosphonitrile dichloride from the mixture.

5 Claims, No Drawings

U.S. PATENT DOCUMENTS

| | | | |
|---|---|---|---|
| 5,914,388 A * | 6/1999 | Allcock et al. | 528/399 |
| 6,020,081 A * | 2/2000 | Raith et al. | 428/704 |
| 6,403,755 B1 * | 6/2002 | Stewart et al. | 528/287 |
| 6,800,672 B2 * | 10/2004 | Dang et al. | 523/113 |
| 2004/0146443 A1 * | 7/2004 | Kuwata | 423/300 |

FOREIGN PATENT DOCUMENTS

| | | |
|---|---|---|
| FR | 2 700 170 | 7/1994 |
| JP | 49-47500 | 5/1974 |
| JP | 51-21000 | 2/1976 |
| JP | 57-3705 | 1/1982 |
| JP | 60-155187 | 8/1985 |
| JP | 62-39534 | 2/1987 |
| JP | 64-87634 | 3/1989 |
| JP | 1-246292 | 10/1989 |
| JP | 2000-198793 | 7/2000 |
| JP | 2001-2691 | 1/2001 |
| RU | 385980 | 9/1973 |

* cited by examiner

PROCESS FOR PRODUCING PHOSPHONITRILIC ACID ESTER

This application is based on and hereby claims priority to International Application No. PCT/JP2004/007708 filed on Jun. 3, 2004 and Japanese Application No. 2003-160916 filed on Jun. 5, 2003, the contents of which are hereby incorporated by reference.

TECHNICAL FIELD

The present invention relates to a method for preparing a phosphonitrilic acid ester from a phosphonitrile dichloride. More specifically, the present invention relates to a method for preparing a phosphonitrilic acid ester by reacting a phosphonitrile dichloride with a phenolic compound and/or an alcoholic compound wherein the reaction is accelerated by the addition of a catalyst thereby preparing the phosphonitrilic acid ester very rapidly.

BACKGROUND ART

A phosphonitrilic acid ester has a very wide range of application as a plastic and its additive, rubber, fertilizer, medicine, etc. Particularly, derivatives of a phosphonitrilic acid ester oligomer or a phosphonitrilic acid ester polymer have very excellent characteristics such as excellent flame retardancy, higher anti-hydrolysis property and higher heat resistance when compared to conventional phosphate esters. Therefore, such derivatives of a phosphonitrilic acid ester oligomer or a phosphonitrilic acid ester polymer have a very promising application in flame retardant and nonflammable materials with respect to imparting flame retardancy and incombustibility to a plastic by a non halogen flame retardant agent, which in recent years has attracted increased social interest. Furthermore, because a resin composition to which they are added shows a very low dielectric constant, industrialization is strongly desired as a flame retardant agent for use in an electronic material such as a printed circuit board material and a semiconductor sealing material.

Among phosphonitrilic acid esters, cyclic trimers represented by the following general formula (7) and cyclic tetramers represented by the following general formula (8) are particularly attracting attention in recent years.

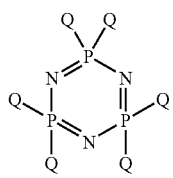
(7)

(wherein Q represents an aryloxy group or an alkoxy group)

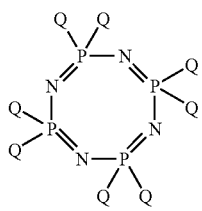
(8)

(wherein Q represents an aryloxy group or an alkoxy group)

The phosphonitrilic acid ester represented by the following general formula (9) does not contain a chlorine atom (hereinafter referred to as a chloro group) bonded to a phosphorus atom in the structural formula. However, since it is usually prepared by alkoxylation or aryloxylation, there remains a monochloro compound having a chloro group as represented by the following general formula (10) in the products obtained by aryloxylation and/or alkoxylation reaction. It is very difficult to replace all the chloro groups by an aryloxy group and/or an alkoxy group at the time of preparation, and it is particularly difficult to replace one chloro group which remained in the last in a molecule.

(9)

(wherein Q represents an aryloxy group or an alkoxy group, and m represents an integer of 3 or more)

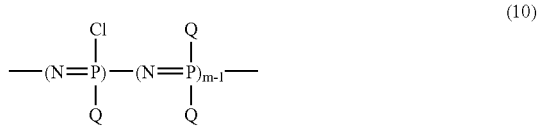
(10)

(wherein Q represents an aryloxy group or an alkoxy group, and m represents an integer of 3 or more)

The remaining chloro group may be hydrolyzed and generate a hydroxy compound represented by the following general formula (11). This may cause an increase in the acid value of the reaction product, or generate a P—O—P bond by a cross-linking reaction to form a gel, and the excellent characteristics which the phosphonitrilic acid ester has may not be exhibited.

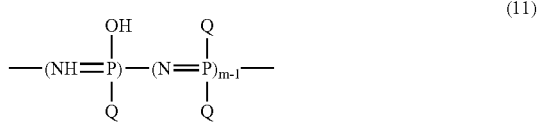
(11)

(wherein Q represents an aryloxy group or an alkoxy group, and m represents an integer of 3 or more)

For example, when a phosphonitrilic acid ester in which substitution on the aryloxy group and/or alkoxy group have not completed is added as a flame retardant agent to a resin such as a polyester resin, particularly a polycarbonate resin that is easily decomposed with an acid, the resin itself may be decomposed by phosphate traces derived from P—OH portions contained in the phosphonitrilic acid ester. In connection with this, not only thermal properties such as flame retardancy and heat resistance of the resin composition but various mechanical physical properties will be impaired. Furthermore, in the case of a resin for use in electronic materials, problems such as reduced dielectric performance may occur.

The method for preparing a phosphonitrilic acid ester includes (1) a method in which a a metal chloride or a solvent, if needed (for example, see JP-A-51-21000). This method reduces unreacted chloro groups that remain in a phosphonitrilic acid ester. However, there arises a problem when a glycidyl group in the epoxy compound opens a ring and reacts with the phosphonitrile dichloride, chloro atoms remain in the molecule. Furthermore, there is also a problem that the epoxy compound does not sufficiently react by itself with the phosphonitrile dichloride, and in order to complete the reaction, the amine compound must be used, and the reaction process and operation become cumbersome.

A method is known in which toluene is used as a reaction solvent and a cyclic phosphonitrile dichloride is reacted with an alkaline metal arylate while adding thereto a linear or cyclic nitrogen-containing organic compound to enhance nucleophilic reactivity, thereby lowering the amount of residual chlorine below 0.01 mass % (for example, see JP-A-2001-2691). According to this method, it is possible to reduce the amount of residual chlorine in a phosphonitrilic acid ester. However, a large amount of the nitrogen-containing organic compound is required, which entails a cumbersome operation of collecting the nitrogen-containing organic compound from the reaction product or the solvent and this makes the method disadvantageous for industrial, application.

There is also a known method in which dioxane phosphonitrile dichloride is reacted with an alkaline metal salt of a hydroxy compound, (2) a method in which a hydroxyl compound is reacted with a phosphonitrile dichloride using a tertiary amine as a hydrochloric acid trapping agent, and (3) a method in which a phase-transfer catalyst such as a quaternary ammonium salt is used and a hydroxy compound and a phosphonitrile dichloride are reacted in the presence of a hydrochloric acid trapping agent such as a secondary or tertiary amine.

Among the related art processes for the preparation a phosphonitrilic acid ester, there is commonly known method in which toluene or xylene is used as an inactive solvent for the reaction, and a phosphonitrile dichloride is made to act on an alkaline metal alcoholate or an alkaline metal phenolate prepared by azeotropic dehydration from an alcoholic compound or a phenolic compound with a hydroxide of an alkaline metal thereby preparing a phosphonitrilic acid ester (for example, see U.S. Pat. No. 4,107,108). This method, however, has a problem where it is difficult to replace all the chloro groups in a phosphonitrile dichloride, for example, by a bulky phenoxy group, where the reaction takes a long time and results in a high content of monochloro compounds.

Another method is known in which a phosphonitrile dichloride, an epoxy compound, and an amine compound react together using a catalyst such as is used as a reaction solvent and an amine-type phase-transfer catalyst and a pyridine derivative as an agent for trapping a hydrogen halide generated in the aryloxylation or alkoxylation are added for the reaction (for example, see JP-A-64-87634). However, this method takes a long time for completing the reaction. In addition, although the pyridine derivative used in a large amount is expensive and desirably to be re-used, it changes to a hydrogen halide salt after the reaction and needs a cumbersome regeneration processes such as an alkali treatment and distillation, which is problematic.

There are additional methods in which toluene as a reaction solvent and a quaternary ammonium salt as a phase-transfer catalyst are used (for example, see JP-A-64-87634, JP-A-60-155187). These methods use a quaternary ammonium salt in a large amount and the operation of collecting the quaternary ammonium salt is cumbersome. Moreover, since a lot of water is used at the time of a reaction, the reaction system is a biphasic system of water and an organic solvent, and phosphonitrile dichloride tends to undergo hydrolysis and the reaction temperature cannot be raised. Therefore, a long time is needed for completion of the reaction. On the other hand, when the reaction temperature is raised in order to enhance the reactivity, the following problems arise such as hydrolysis becomes noticeable, phosphate traces derived from P—OH portions generate and gelling tends to take place by a cross-linking reaction.

There is also a known method in which monochlorobenzene is used as a reaction solvent, and a cyclic phosphonitrile dichloride and an alkaline metal arylate and/or an alkaline metal alcoholate are reacted while the amount of moisture in the reaction system is controlled (for example, see JP-A-2000-198793). This method allows particles of the alkaline metal arylate and the alkaline metal alcoholate in the reaction solvent to be finely dispersed by reducing the amount of moisture at the time of preparing the alkaline metal arylate and the alkaline metal alcoholate, and thereby improves the reactivity. However, such improvement in the reactivity is still insufficient and the reaction time is long until completion.

There is a known method in which an aliphatic hydrocarbon having 6 to 9 carbon atoms is used as a reaction solvent and an alkaline metal alcoholate is prepared from an alkaline metal and an alcohol and then reacted with a phosphonitrile dichloride dissolved in monochlorobenzene (for example, see U.S. Pat. No. 3,939,228). It is possible to complete the reaction in a relatively short reaction time in this reaction. However, an alkaline metal is expensive and difficult to handle since it has very high reactivity with moisture, and therefore it is problematic when applied to industrial uses.

Furthermore, there is a known method in which dichlorobenzene or trichlorobenzene is used as a reaction solvent, and an alkaline metal arylate or an alkaline metal alcoholate are reacted with a phosphonitrile dichloride polymer (for example, see French patent No. 2,700,170). In this method, there is no description about the amount of moisture in the reaction system at the time of an aryloxylation and/or an alkoxylation reaction, and, according to studies of the present inventors, there is a problematic decrease in the reactivity and a problematic hydrolysis of the phosphonitrile dichloride.

In the meantime, there is a known method for preparing phosphonitrilic acid ester in which the reaction solvent is not distilled off from the reaction solution that contains a phosphonitrile dichloride prepared from a phosphorus chloride and ammonium chloride and subjected to a reaction with an alcoholic compound and/or a phenolic compound as it is.

Moreover, methods for synthesizing a phosphonitrile dichloride used as main materials at the time of preparing a phosphonitrilic acid ester include (1) a method using phosphorus pentachloride, (2) a method using phosphorus trichloride, (3) a method using white phosphorus, and (4) a method using phosphorus nitride as a phosphorus source.

Extensive studies have been made with regard to the preparation method of a phosphonitrile dichloride for many years. As a typical technique, there is a known method in which phosphorus pentachloride and ammonium chloride are reacted in the presence of a multivalent metal compound catalyst, and the products containing a cyclic phosphonitrile dichloride oligomer is collected (for example, see JP-A-57-3705). In addition, there is a known method in which ammonia gas and hydrogen chloride gas are introduced into the reaction system to produce particulate ammonium chloride, which is then reacted with a phosphorus chloride to prepare a cyclic phosphonitrile dichloride (for example, see JP-A-49-47500). Furthermore, there is a known method in which a multivalent metal compound having Lewis acidity and a pyridine derivative such as quinoline are used as a catalyst and phosphorus pentachloride and ammonium chloride are reacted to selectively prepare a trimer (for example, see JP-A-62-39534).

From the prepared phosphonitrile dichloride, excessive ammonium chloride is removed usually by filtering the reaction slurry containing the phosphonitrile dichloride. Then, at least one operation step selected from the isolating steps described below are performed to isolate or purify the phosphonitrile dichloride from the reaction solution, and a product isolated or purified is used as a material of the following second step reaction, i.e., alkoxylation or aryloxylation reaction.

1) an operation in which the solvent is evaporated from the reaction solution and the crystal component deposited by condensing it (mainly composed of lower molecular weight cyclic compounds having m of 3 or 4 in the following general formula (12)) is separated by centrifugal separation, filtration, etc.;
2) an operation in which the solvent is evaporated from the reaction solution and linear and cyclic compounds are separated by adding a hydrocarbon solvent to the condensed or dried component;
3) an operation in which the reaction solution is contacted with water thereby extracting linear compounds in the aqueous phase;
4) an operation in which the content of the cyclic compounds having m of 3 or 4 in the following general formula (12) is increased by recrystalization purification or sublimation purification.

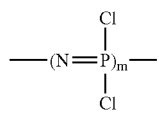

(12)

(wherein m represents an integer of 3 or more)

There are known examples of the above method in which the reaction solvent is not distilled off from the reaction solution that contains a phosphonitrile dichloride prepared from a phosphorus chloride, which phosphonitrile dichloride is reacted with an alcoholic compound and/or a phenolic compound. For example, in one method, monochlorobenzene is used as a reaction solvent and an alcohol and cyclic phosphonitrile dichloride are reacted in the presence of a pyridine derivative (for example, see U.S. Pat. No. 3,794,701). However, this method takes a long time for completing the reaction and the pyridine derivative used in a large amount is expensive and the recovery and the regeneration processes are cumbersome.

There is also a known method in which a linear phosphonitrile dichloride is prepared from the reaction of phosphorus pentachloride and ammonium chloride in a chlorine containing unsaturated hydrocarbon and an alcohol is made acted on the reaction solution thereby preparing a polyalkoxyphosphazene (for example, see Russian patent No. 385,980). In this method, straight chain unsaturated chlorinated hydrocarbons are the only described reaction solvent, but the industrial use may be a problem since some of these unsaturated chlorinated hydrocarbons are carcinogenic. Moreover, since the ammonium chloride does not contain an alkaline metal alcoholate but an alcohol is used at the time of the alkoxylation reaction of the phosphonitrile dichloride, the reactivity is very low, and it takes a long time for completing the reaction. Also in this technique, there is no description about the amount of moisture in the reaction system, and according to studies of the present inventors, there is a problem that moisture decreases the reactivity and the hydrolysis of the phosphonitrile dichloride.

DISCLOSURE OF THE INVENTION

Under these circumstances, an object of the present invention is to provide a method for preparing a cyclic and/or linear phosphonitrilic acid ester from a cyclic and/or linear phosphonitrile dichloride wherein the phosphonitrilic acid ester contains very little monochloro compound and is prepared in a shorter reaction time.

Accordingly, the inventors have conducted intensive researches to achieve the above described purpose, i.e., on the preparation method for reducing the amount of a monochloro compound contained in a phosphonitrilic acid ester in a short reaction time and have consequently found that the reaction is accelerated and completed rapidly surprisingly by using a certain specific compound as a reaction catalyst and controlling the amount of moisture in the reaction system in preparing the phosphonitrilic acid ester by reacting a phosphonitrile dichloride with a phenolic compound and/or an alcoholic compound. Further surprisingly, the second step reaction is accelerated by very small amount of a metal ingredient contained in the first step reaction solution containing the phosphonitrile dichloride, without isolating the phosphonitrile dichloride prepared by the reaction of a phosphorus chloride and ammonium chloride from the reaction slurry. Consequently, the inventors have found that the phosphonitrilic acid ester in which the content of the monochloro compound is very little can be obtained very rapidly, and completed the present invention.

That is, the present invention has the following features.

[1] A method for preparing a cyclic and/or linear phosphonitrilic acid ester represented by

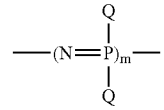

(5)

where Q represents an aryloxy group or an alkoxy group and m represents an integer of 3 or more, the method comprising:

reacting a cyclic and/or linear phosphonitrile dichloride with at least one compound selected from a phenolic compound and an alcohol compound in the presence of a reaction solvent, wherein:

the cyclic and/or linear phosphonitrile dichloride is represented by the formula (1)

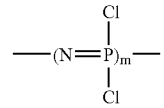

(1)

where m represents an integer of 3 or more,
the phenolic compound is represented by formula (2) or (3)

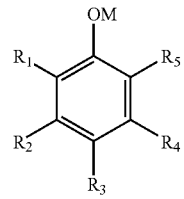

(2)

where M is a hydrogen atom or an alkaline metal, $R_1$ to $R_5$ are any of a hydrogen atom, an OM group, an aliphatic hydrocarbon group having 1 to 10 carbon atoms and an aromatic hydrocarbon group having 6 to 10 carbon atoms, and adjacent groups in $R_1$ to $R_5$ may form a ring

(3)

where M is a hydrogen atom or an alkaline metal, and $R_6$ is an aliphatic hydrocarbon group having 1 to 10 carbon atoms or an aromatic hydrocarbon group having 6 to 10 carbon atoms, the alcohol compound is represented by the following general formula (4)

$$R_7\text{O-M} \qquad (4)$$

where M is a nyarogen atom or an alkaline metal, and R7 is an aliphatic hydrocarbon group having 1 to 10 carbon atoms, (i) the reaction solvent is at least one solvent selected from aromatic hydrocarbons and halogenated hydrocarbons, and (ii) the reaction is performed in the presence of a catalyst represented by the formula (6)

$$(\text{NH}_4)_p A_q X_r \qquad (6)$$

where A is an element from one of groups IIA, IIIA, IVA, VA, IIB, IIIB, IVB, VB, VIB, VIIB and VIII in the long periodic table, X represents a halogen atom; p is an integer of 0 to 10, q is an integer of 1 to 10 and r is an integer of 1 to 35.

[2] The method according to the above [1], wherein an alkaline metal salt of a phenolic compound and/or an alcohol compound is selected from at least one of a phenolic compound represented by the formula (2) or (3) and an alcohol compound represented by the formula (4).

[3] The method according to the above [1] or [2], wherein the catalyst is a compound of the formula (6) in which p=0.

[4] The method according to the above [1] or [2], wherein the catalyst is a compound of the formula (6) in which p=1 to 10.

[5] The method according to according to any one of the above [1] to [4], wherein the catalyst is a compound of the formula (6) in which A is Mg, Al, Cr, Co, Cu or Zn.

[6] The method according to according to any one of the above [1] to [5], wherein the reaction solvent used for preparing the phosphonitrilic acid ester is selected from at least one toluene, xylene, monochlorobenzene, dichlorobenzene and trichlorobenzene.

[7] The method according to according to any one Of the above [1 ] to [6 ], wherein the amount of moisture In the reaction system is 0.2 mol or less per mol of phosphonitrile dichloride.

[8] A method for preparing a cyclic and/or linear phosphonitrilic acid ester represented by the formula (5)

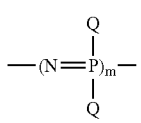
(5)

(wherein Q represents an aryloxy group or an alkoxy group and m represents an integer of 3 or more), the method comprising:

reacting a cyclic and/or linear phosphonitrile dichloride represented by the formula (1)

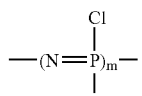
(1)

(wherein m represents an integer of 3 or more), with at least one selected from a phenolic compound represented by the following general formula (2) or (3)

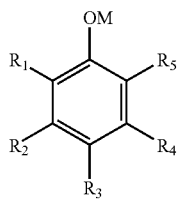
(2)

(wherein M is a hydrogen atom or an alkaline metal, $R_1$ to $R_5$ are any of a hydrogen atom, an OM group, an aliphatic hydrocarbon group having 1 to 10 carbon atoms and an aromatic hydrocarbon group having 6 to 10 carbon atoms, and adjacent groups in $R_1$ to $R_5$ may form a ring) or

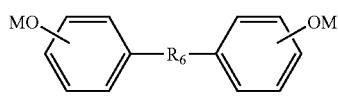
(3)

(wherein M is a hydrogen atom or an alkaline metal, and $R_6$ is an aliphatic hydrocarbon group having 1 to 10 carbon atoms or an aromatic hydrocarbon group having 6 to 10 carbon atoms), and an alcohol compound represented by the formula (4)

$$R_7\text{O-M} \qquad (4)$$

(wherein M is a hydrogen atom or an alkaline metal, and R7 is an aliphatic hydrocarbon group having 1 to 10 carbon atoms), in the presence of a reaction solvent, wherein:

the solid component in the reaction slurry obtained in the preparation of the phosphonitrile dichloride is used as a catalyst.

[9] The method according to the above [8], wherein an alkaline metal salt of a phenolic compound and/or an alcohol compound is selected from at least one of a phenolic compound represented by the formula (2) or (3) and an alcohol compound represented by the formula (4).

[10] The method according to the above [8] or [9], wherein the solid component is a component contained in the reaction slurry obtained by reacting a phosphorus chloride with ammonium chloride in the presence of a reaction catalyst using ammonium chloride in an amount in excess of the phosphorus chloride in the preparation of the phosphonitrile dichloride.

[11] The method according to according to any one of the above [8] to [10], wherein the reaction solvent used for preparing the phosphonitrilic acid ester is selected from at least one toluene, xylene, monochlorobenzene, dichlorobenzene and trichlorobenzene.

[12] The method according to according to any one of the above [8] to [11], wherein the amount of moisture in the reaction system is 0.2 mol or less per mol of the phosphonitrile dichloride.

[13] A method for preparing a cyclic and/or linear phosphonitrilic acid ester represented by the formula (5)

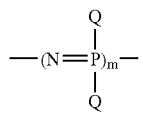

(wherein Q represents an aryloxy group or an alkoxy group and m represents an integer of 3 or more), the method comprising:

a firs step reaction which prepares a phosphonitrile dichloride represented by the formula (1)

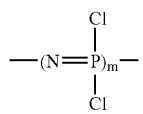

(wherein m represents an integer of 3 or more), by using a halogenated aromatic hydrocarbon as a reaction solvent and reacting a phosphorus chloride with ammonium chloride in the presence of a catalyst, and a second step reaction which prepares the cyclic and/or linear phosphonitrilic acid ester represented by the formula (5) by reacting the phosphonitrile dichloride prepared in the first step reaction with a phenolic compound represented by the formula (2)

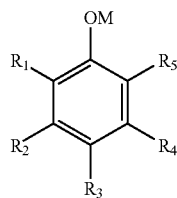

(wherein M is a hydrogen atom or an alkaline metal, $R_1$ to $R_5$ are any of a hydrogen atom, an OM group, an aliphatic hydrocarbon group having 1 to 10 carbon atoms and an aromatic hydrocarbon group having 6 to 10 carbon atoms, and adjacent groups in $R_1$ to $R_5$ may form a ring) or (3)

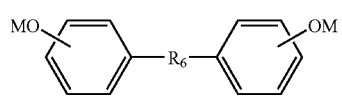

(wherein M is a hydrogen atom or an alkaline metal, and $R_6$ is an aliphatic hydrocarbon group having 1 to 10 carbon atoms or an aromatic hydrocarbon group having 6 to 10 carbon atoms) and an alcohol compound represented by the following general formula (4)

$$R_7O\text{-}M \qquad (4)$$

(wherein M is a hydrogen atom or an alkaline metal, and $R_7$ is an aliphatic hydrocarbon group having 1 to 10 carbon atoms), without isolating the phosphonitrile dichloride from the reaction slurry prepared in the first step reaction.

[14] The method according to the above [13], wherein an alkaline metal salt of a phenolic compound and/or an alcohol compound is selected from at least one of a phenolic compound represented by the formula (2) or (3) and an alcohol compound represented by the formula (4).

[15] The method according to the above [13] or [14], wherein the catalyst used for the first step reaction is selected from at least one of metal oxides and metal chlorides.

[16]. The method according to any one of the above [13] to [15], wherein the catalyst used for the first step reaction is selected from at least one of zinc oxide, magnesium oxide, aluminum oxide, cobalt oxide, copper oxide, zinc chloride, magnesium chloride, aluminum chloride, cobalt chloride, copper chloride, and zinc chloride.

[17] The method according to any one of the above [13] to [16], wherein the halogenated aromatic hydrocarbon is selected from at least one of monochlorobenzene, dichlorobenzene and trichlorobenzene.

[18] The method according to any one of the above [13] to [17], wherein the second step reaction is conducted without isolating any solid component from the reaction slurry in the first step reaction.

[19] The method according to any one of the above [13] to [18], wherein the metal derived from the catalyst in the reaction mixture is mainly composed of the phosphonitrile dichloride prepared in the first step reaction is present in an amount of $1 \times 10^{-6}$ mol or more per mol of the phosphonitrile dichloride.

[20] The method according to any one of the above [13] to [19], wherein the amount of moisture in the reaction system in the second step reaction is 0.2 mol or less per mol of the phosphonitrile dichloride According to the method for preparing a phosphonitrilic acid ester of the present invention, it is possible to prepare a phosphonitrilic acid ester in which the content of the monochloro compound is very little by using a certain specific compound as a reaction catalyst in preparing the phosphonitrilic acid ester by reacting a cyclic and/or linear phosphonitrile dichloride with a phenolic compound and/or an alcohol compound. Furthermore, it is possible to prepare a phosphonitrilic acid ester very rapidly by reacting a phosphonitrile dichloride that is prepared by the reaction of a phosphorus chloride and ammonium chloride, the phosphonitrile compound being reacted in the presence of a catalyst with a phenolic compound and/or an alcohol compound in a halogenated aromatic hydrocarbon solvent without isolating the phosphonitrile dichloride from the reaction slurry.

Moreover, according to the present invention, since the reaction proceeds very rapidly, the reaction time can be shortened and it is possible to reduce the production cost and to prepare a phosphonitrilic acid ester with decreased costs. Accordingly, the present invention enables preparation of an industrially useful phosphonitrilic acid ester with a low monochloro compound content, improved anti-hydrolysis and heat resistance of the phosphonitrilic acid ester itself, and further suppresses degeneration of physical properties of a resin composition. Therefore, it can be expected that various derivatives of a phosphonitrilic acid ester oligomer or a phosphonitrilic acid ester polymer can be used to wide range of applications such as a plastic and its additive, rubber, fertilizer, medicine, etc.

BEST MODE FOR CARRYING OUT THE INVENTION

Hereinbelow, the present invention is explained. First, terms used in the present invention are explained.

In the present invention, the preparation of a phosphonitrile dichloride from a phosphorus chloride and ammonium chloride is referred to as the first step reaction. The second step reaction refers to a reaction which prepares a phosphonitrilic acid ester from the phosphonitrile dichloride and a phenolic compound and/or an alcohol compound. A catalyst used in the first step reaction is referred to as a catalyst for the first step reaction, and a component insoluble to the reaction solution in the reaction slurry obtained from the first step reaction is referred to as a solid component. In addition, a catalyst used in the second step reaction is referred to as a catalyst for the second step reaction.

From a viewpoint of the features thereof, the present invention can be considered as divided into three groups:

(I) a specific compound is used as a catalyst in preparing a phosphonitrilic acid ester from a phosphonitrile dichloride and a phenolic compound and/or an alcohol compound;

(II) a component insoluble to the reaction solution obtained from the first step reaction (solid component) is used as a catalyst in preparing a phosphonitrilic acid ester from a phosphonitrile dichloride and a phenolic compound and/or an alcohol compound; and (III) the reaction slurry obtained from the first step reaction without isolating a phosphonitrile dichloride from the slurry is fed to the second step reaction in preparing a phosphonitrilic acid ester.

Hereinbelow, each of these above-mentioned groups (I) to (III) of the present invention is described. Constitution (I) is described first.

A compound used as a catalyst for the second step reaction in the group (I) of the present invention is represented by the above described general formula (6).

$(NH_4)_p A_q X_r$ (6)

(wherein X represents a halogen atom and p is an integer of 0 to 10 and q is an integer of 1 to 10 and r is an integer of 1 to 35)

In addition, in the formula, A is an element of groups IIA, IIIA, IVA, VA, IIB, IIIB, IVB, VB, VIIB and VIIB or VIII. Examples include Mg, Ca, Sr, Ba, Sc, Y, Ti, Zr, V, Nb, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, La, Ce, Pr, Nd, Pm, Sm, Eu, Gd, Tb, Dy, Ho, Er, Tm, Yb, Lu, and among these, Mg, Cr, Mn, Fe, Co, Ni, Cu, Zn, Cd, Al, Ga, Si, La, Ce, Pr, Nd, Sm, Gd, Dy, Ho and Er or Yb is preferred, and Mg, Al, Co, Cu, Zn or Gd is more preferred, and Mg, Co, Cu, or Zn is particularly preferred.

More specifically, the catalyst is preferably $MgCl_2$, $NH_4MgCl_3$, $AlCl_3$, $NH_4AlCl_5$, $(NH_4)_2AlCl_5$, $(NH_4)_3AlCl_6$, $CrCl_3$, $NH_4CrCl_4$, $(NH_4)_2CrCl_5$, $(NH_4)_3CrCl_6$, $MnCl_2$, $MnCl_3$, $NH_4MnCl_3$, $NH_4MnCl_4$, $(NH_4)_2MnCl_4$, $(NH_4)_3MnCl_6$, $(NH_4)_6MnCl_8$, $FeCl_2$, $FeCl_3$, $NH_4FeCl_3$, $NH_4FeCl_4$, $(NH_4)_2Fe_2Cl_6$, $(NH_4)_2FeCl_5$, $(NH_4)_3FeCl_6$, $CoCl_2$, $NH_4CoCl_3$, $(NH_4)_2CoCl_4$, $(NH_4)_3CoCl_5$, $NiCl_2$, $NH_4NiCl_3$, $(NH_4)_2NiCl_4$, $CuCl$, $CuCl_2$, $NH_4CuCl_3$, $(NH_4)_2CuCl_4$, $ZnCl_2$, $NH_4ZnCl_3$, $(NH_4)_2ZnCl_4$, $(NH_4)_3ZnCl_5$, $GaCl_3$, $NH_4GaCl_4$, $(NH_4)_2GaCl_5$, $(NH_4)_3GaCl_6$, $LaCl_3$, $(NH_4)_2LaCl_5$, $(NH_4)_3LaCl_6$, $GdCl_3$, $NH_4GdCl_4$, $(NH_4)_2GdCl_5$ and $(NH_4)_3GdCl_6$ and particularly preferable are $MgCl_2$, $NH_4MgCl_3$, $CoCl_2$, $NH_4CoCl_3$, $(NH_4)_2CoCl_4$, $(NH_4)_3CoCl_5$, $CuCl$, $CuCl_2$, $NH_4CuCl_3$, $(NH_4)_2CuCl_4$, $ZnCl_2$, $NH_4ZnCl_3$, $(NH_4)_2ZnCl_4$ and $(NH_4)_3ZnCl_5$.

These catalysts may be used alone respectively or two or more may be used in combination in various ratios. The amount of the catalyst used is preferably $10^{-5}$ to 1 mol, more preferably $5 \times 10^{-5}$ to $10^{-1}$ mol per mol of phosphonitrile dichloride.

Hereinbelow, group (II) is described. The solid component used as a catalyst for the second step reaction in group (II) is a component (solid component) insoluble to the reaction solution after reacting a phosphorus chloride and ammonium chloride in the presence of a catalyst for the first step reaction using ammonium chloride in an amount in excess of the phosphorus chloride in the preparation reaction of a phosphonitrile dichloride.

It is common to raise the content of a cyclic phosphonitrile dichloride oligomer by isolating a phosphonitrile dichloride by removing the solid component and the reaction solvent from the reaction slurry after the first step reaction and by further performing distillation, recrystalization, etc.

A compound used as the above described first step reaction catalyst is a metal oxide or a metal chloride and examples of the metal include Mg, Ca, Sr, Ba, Sc, Y, Ti, Zr, V, Nb, Cr, Mo, Mn, Fe, Ru, Co, Rh, Ir, Ni, Pd, Pt, Cu, Ag, Au, Zn, Cd, Hg, Al, Ga, In, Tl, Si, Ge, Sn, Pb, La, Ce, Pr, Nd, Pm, Sm, Eu, Gd, Tb, Dy, Ho, Er, Tm, Yb, Lu and among these, Mg, Cr, Mn, Fe, Co, Ni, Cu, Zn, Cd, Al, Ga, In, Si, La, Ce, Pr, Nd, Sm, Gd, Dy, Ho, Er and Yb are preferred. Furthermore, among these, zinc oxide, magnesium oxide, aluminum oxide, cobalt oxide, copper oxide, zinc chloride, magnesium chloride, aluminum chloride, cobalt chloride, copper chloride and zinc chloride are preferred, and zinc oxide and zinc chloride are particularly preferred.

These catalysts may be used alone respectively or two or more may be used in combination. The amount of the catalyst used for the first step reaction is preferably $10^{-5}$ to 1 mol, more preferably $10^{-3}$ to $10^{-1}$ mol per mol of phosphonitrile dichloride.

The component (solid component) insoluble to the reaction solution after the above described first step reaction is a solid component isolated from the reaction slurry. Although the details about this solid component are unknown, it is presumed that it consists of excessive ammonium chloride and catalytic ingredients used at the time of the preparation of a phosphonitrile dichloride. There is no particular limitation in the method of isolating the solid component from the reaction solution, and it can be carried out by any conventionally known method for separating solid and liquid such as filtration under reduced pressure, pressure filtration, centrifugal separation and decantation, at an ordinary temperature or while heated.

The solid component isolated from the reaction slurry may be stored as it is, or may be used at the time of preparing a phosphonitrilic acid ester, and it may be dried and stored. There is no particular limitation in the method of drying the solid component, and for example, includes a method of drying at 20 to 150° C. for about several hours using a hot air dryer or a vacuum dryer. Since the solid component contains ammonium chloride as the main ingredient and has hygroscopicity, it is preferable to store under atmosphere with low humidity.

In groups (I) and (II), although there is no particular limitation in the method of putting the catalyst for the second step reaction into the reaction system, it may be put into the liquid in which a phenolic compound and/or an alcohol compound is dissolved or dispersed in a reaction solvent or may be put into the liquid in which a phosphonitrile dichloride is dissolved in a reaction solvent.

Further in the groups (I) and (II), pyridine, quinoline and derivatives thereof can be used together in addition to the catalyst for the second step reaction as a conventionally known method. Examples of the pyridine derivative include 2-hydroxypyridine, 3-hydroxypyridine, 4-hydroxypyridine, 2,6-dihydroxypyridine, 3-hydroxy-6-methylpyridine, 2-chloropyridine, 3-chloropyridine, 2,6-dichloropyridine, α-picoline, β-picoline, γ-picoline, lutidine, methylethylpyridine. Examples of the quinoline derivative includes 2-methylquinoline, 3-methylquinoline, 4-methylquinoline, 5-methylquinoline, 6-methylquinoline, 7-methylquinoline, 8-methylquinoline, 2-chloroquinoline, 3-chloroquinoline, 4-chloroquinoline, 5-chloroquinoline, 6-chloroquinoline, 2,3-dichloroquinoline, 2-methyl-4-bromoquinoline, 3-chloroisoquinoline, 8-chloroisoquinoline. These may be used alone or two or more of them may be used in combination.

A phosphonitrile dichloride used as a material in groups (I) and (II) may be cyclic or may be linear. There is no particular limitation in the composition, i.e., the ratio of a cyclic trimer in which m is 3, a cyclic tetramer in which m is 4 and cyclic polymers and linear compounds in which m≧5 in the above described general formula (1), and a mixture which contains each ingredient at any ratio can be used. The preparation method of a phosphonitrile dichloride is not particularly limited, but a phosphonitrile dichloride prepared by any kind of method can be used. For example, a phosphonitrile dichloride containing a cyclic and linear compounds which were prepared from ammonium chloride and phosphorus pentachloride or ammonium chloride and phosphorus trichloride and chlorine can be used. A cyclic phosphonitrile dichloride obtained by processing a phosphonitrile dichloride with a hydrocarbon system solvent, and removing linear compounds may be used if needed. A phosphonitrile dichloride having a higher content of a cyclic trimer and tetramer by recrystalization purification or sublimation purification may be used.

In addition, a phenolic compound in the present invention refers to a monovalent phenolic compound represented by the above described general formula (2) and/or a divalent phenolic compound represented by the above described general formula (3).

Specific examples of the monovalent phenolic compound in which M is a hydrogen atom, include phenol, 1-naphtol, 2-naphtol, 4-phenylphenol, o-cresol, m-cresol, p-cresol, o-ethylphenol, m-ethylphenol, p-ethylphenol, o-propylphenol, m-propylphenol, p-propylphenol, o-isopropylphenol, m-isopropylphenol, p-isopropyliphenol, o-butylphenol, m-butylphenol, p-butylphenol, o-(2-methylpropyl)phenol, m-(2-methylpropyl)phenol, p-(2-methylpropyl)phenol, o-t-butylphenol, m-t-butylphenol, p-t-butylphenol, o-pentylphenol, m-pentylphenol, p-pentylphenol, o-(2-methylbutyl)phenol, m-(2-methylbutyl)phenol, p-(2-methylbutyl)phenol, o-(3-methylbutyl)phenol, m-(3-methylbutyl)phenol, p-(3-methylbutyl)phenol, o-t-amylphenol, m-t-amylphenol, p-t-amylphenol, 1-hydroxy-2-methylnaphthalene, 1-hydroxy-3-methylnaphthalene, 1-hydroxy-4-methylnaphthalene, 1-hydroxy-5-methylnaphthalene, 1-hydroxy-6-methylnaphthalene, 1-hydroxy-7-methylnaphthalene, 1-hydroxy-8-methylnaphthalene, 2-ethyl-1-hydroxynaphthalene, 3-ethyl-1-hydroxynaphthalene, 4-ethyl-1-hydroxynaphthalene, 5-ethyl-1-hydroxynaphthalene, 6-ethyl-1-hydroxynaphthalene, 7-ethyl-1-hydroxynaphthalene, 8-ethyl-1-hydroxynaphthalene, 2-hydroxy-1-methylnaphthalene, 2-hydroxy-3-methylnaphthalene, 2-hydroxy-4-methylnaphthalene, 2-hydroxy-5-methylnaphthalene, 2-hydroxy-6-methylnaphthalene, 2-hydroxy-7-methylnaphthalene, 2-hydroxy-8-methylnaphthalene, 1-ethyl-2-hydroxynaphthalene, 3-ethyl-2-hydroxynaphthalene, 4-ethyl-2-hydroxynaphthalene, 5-ethyl-2-hydroxynaphthalene, 6-ethyl-2-hydroxynaphthalene, 7-ethyl-2-hydroxynaphthalene, 8-ethyl-2-hydroxynaphthalene, 2-methyl-4-phenylphenol, 2-ethyl-4-phenylphenol, 2,3-xylenol, 2,4-xylenol, 2,5-xylenol, 2,6-xylenol, 3,4-xylenol, 3,5-xylenol, 2-ethyl-6-methylphenol, 3-ethyl-6-methylphenol, 4-ethyl-6-methylphenol, 5-ethyl-6-methylphenol, 2-ethyl-3-methylphenol, 2-ethyl-4-methylphenol, 2-ethyl-5-methylphenol, 3-ethyl-5-methylphenol, 2-methyl-3-n-propylphenol, 2-methyl-4-n-propylphenol, 2-methyl-5-n-propylphenol, 2-methyl-6-n-propylphenol, 3-methyl-2-n-propylphenol, 4-methyl-2-n-propylphenol, 5-methyl-2-n-propylphenol, 3-methyl-4-n-propylphenol, 3-methyl-5-n-propylphenol, 2-methyl-3-isopropylphenol, 2-methyl-4-isopropylphenol, 2-methyl-5-isopropylphenol, 2-methyl-6-isopropylphenol, 3-methyl-2-isopropylphenol, 4-methyl-2-isopropylphenol, 5-methyl-2-isopropylphenol, 3-methyl-4-isopropylphenol, 3-methyl-5-isopropylphenol, 2-butyl-6-methylphenol, 3-n-butyl-6-methylphenol, 4-n-butyl-6-methylphenol, 5-n-butyl-6-methylphenol, 2-n-butyl-3-methylphenol, 2-n-butyl-4-methylphenol, 2-n-butyl-5-methylphenol, 3-n-butyl-4-methylphenol, 3-n-butyl-5-methylphenol, 2-(2-methylpropyl)-6-methylphenol, 2-(2-methylpropyl)-6-methylphenol, 3-(2-methylpropyl)-6-methylphenol, 4-(2-methylpropyl)-6-methylphenol, 5-(2-methylpropyl)-6-methylphenol, 2-(2-methylpropyl)-3-methylphenol, 2-(2-methylpropyl)-4-methylphenol, 2-(2-methylpropyl)-5-methylphenol, 3-(2-methylpropyl)-4-methylphenol, 3-(2-methylpropyl)-5-methylphenol, 2-(3-methylpropyl)-6-methylphenol, 3-(3-methylpropyl)-6-methylphenol, 4-(3-methylpropyl)-6-methylphenol, 5-(3-methylpropyl)-6-methylphenol, 2-(3-methylpropyl)-3-methylphenol, 2-(3-methylpropyl)-4-methylphenol, 2-(3-methylpropyl)-5-methylphenol, 3-(3-methylpropyl)-4-methylphenol, 3-(3-methylpropyl)-5-methylphenol, 2-t-butyl-6-methylphenol, 3-t-butyl-6-methylphenol, 4-t-butyl-6-methylphenol, 5-t-butyl-6-methylphenol, 2-t-butyl-3-methylphenol, 2-t-butyl-4-methylphenol, 2-t-butyl-5-methylphenol, 3-t-butyl-4-methylphenol, 3-t-butyl-5-methylphenol, 2,3-diethylphenol, 2,4-diethylphenol, 2,5-diethylphenol, 2,6-diethylphenol, 3,4-diethylphenol, 2,3-di-n-propylphenol, 2,4-di-n-propylphenol, 2,5-di-n-propylphenol, 2,6-di-n-propylphenol, 3,5-di-n-propylphenol, 2,3-di-isopropylphenol, 2,4-di-isopropylphenol, 2,5-di-isopropylphenol, 2,6-di-isopropylphenol, 3,4-di-isopropylphenol, 3,5-di-isopropylphenol, 2,3-di-t-butylphenol, 2,4-di-t-butylphenol, 2,5-di-t-butylphenol, 2,6-di-t-butylphenol, 3,4-di-t-butylphenol, 3,5-di-t-butylphenol, 2,3-di-t-amylphenol, 2,4-di-t-amylphenol, 2,5-di-t-amylphenol, 2,6-di-t-amylphenol, 3,4-di-t-amylphenol, 3,5-di-t-amylphenol, 1-hydroxy-2,3-dimethylnaphtalene, 1-hydroxy-2,5-dimethylnaphtalene, 1-hydroxy-2,6-dimethylnaphtalene, 1-hydroxy-2,7-dimethylnaphtalene, 2-hydroxy-1,3-dimethylnaphtalene, 2-hydroxy-1,5-dimethylnaphtalene, 2-hydroxy-1,7-dimethylnaphtalene, 2-hydroxy-1,8-dimethylnaphtalene, 2,3-diethyl-1-hydroxynaphthalene, 2,5-diethyl-1-hydroxynaphthalene, 2,6-diethyl-1-hydroxynaphthalene, 2,7-diethyl-1-hydroxynaphthalene, 1,3-diethyl-2-hydroxynaphthalene, 1,5-diethyl-2-hydroxynaphthalene, 1,7-diethyl-2-hydroxynaphthalene, 1,8-diethyl-2-hydroxynaphthalene, 2,6-dimethyl-4-phenylphenol and 2,6-diethyl-4-phenylphenol. Among these, phenol, 1-naphthol, 2-naphthol, 4-phenylphenol, o-cresol, m-cresol, p-cresol, 2,3-xylenol, 2,4-xylenol, 2,5-xylenol, 2,6-xylenol, 3,4-xylenol, 3,5-xylenol are preferred.

Among the specific examples of the phenolic divalent compounds described above, for example, 2,2-bis(4'-oxyphenyl) propane (bisphenol A), catechol, 1,2-dihydroxynaphthalene, 1,8-dihydroxynaphthalene, 2,3-dihydroxynaphthalene, 3,4-dihydroxynaphthalene, o,o-biphenol etc. are preferred.

In addition, an alcohol compound in the present invention refers to a compound represented by the above described general formula (4). Specific examples of the alcohol compound in which M is a hydrogen atom include methanol, ethanol, n-propanol, isopropanol, n-butanol, 2-butanol, t-butanol, n-pentanol, 2-methylbutanol, 3-methylbutanol, 4-methylbutanol, 2,2-dimethyipropanol, 3,3-dimethylpropanol, 3-ethyipropanol, n-hexanol, 2-methylpentanol, 3-methylpentanol, 4-methylpentanol, 5-methylpentanol, 2,2-dimethylbutanol, 2,3-dimethylbutanol, 2,4-dimethylbutanol, 3,3-dimethylbutanol, 3,4-dimethylbutanol, 3-ethylbutanol, 4-ethylbutanol, 2,2,3-trimethylpropanoi, 2,3,3-trimethylpropanol, 3-ethyl-2-methyipropanol, 3-isopropyipropanol, n-heptanol and n-octanol.

These phenolic compounds or alcohol compounds may be used alone, or two or more of them may be used in combination at any ratio. When two or more phenolic compounds and alcohol compounds are used, the resulted phosphonitrilic acid ester has naturally two or more aryloxy groups or alkoxy groups.

As for the phenolic compound represented by the above described general formula (2) or (3) and the alcohol compound represented by the general formula (4) used in groups (I) and (II), an alkaline metal salt of a phenolic compound or an alkaline metal salt of an alcohol compound are preferred from a viewpoint of reactivity in the reaction with a phosphonitrile dichloride to prepare the phosphonitrilic acid ester. The alkaline metal used for these alkaline metal salts includes lithium, potassium and sodium.

There is no particular limitation in the preparation method of a metal arylate or metal alcoholate from a phenolic compound or an alcohol compound. For example, an alkaline metal hydroxide such as lithium hydroxide, sodium hydroxide and potassium hydroxide is made to act on a phenolic compound or an alcohol compound, and the generated water is removed under heating or reduced pressure thereby obtaining a metal arylate or metal alcoholate. An organic solvent which may form an azeotropic mixture with the generated water may be added and azeotropic dehydration may be performed while heating. Furthermore, an alkaline metal by itself may be reacted with a phenolic compound or an alcohol compound to obtain a metal arylate or metal alcoholate.

The reaction solvent used in groups (I) and (II) is at least one selected from aromatic hydrocarbons and halogenated hydrocarbons. For example, toluene, ethylbenzene, 1,2-xylene, 1,3-xylene, 1,4-xylene, 1-methyl-2-ethylbenzene, 1-methyl-3-ethylbenzene, 1-methyl-4-ethylbenzene, chloroform, benzene, tetrachloroethane, tetrachloroethylene, monochlorobenzene, 1,2-dichlorobenzene, 1,3-dichlorobenzene, 1,4-dichlorobenzene, 1,2,3-trichlorobenzene, 1,2,4-trichlorobenzene, 1,2,5-trichlorobenzene are preferable, and toluene, xylene, monochlorobenzene, 1,2-dichlorobenzene, 1,3-dichlorobenzene, 1,4-dichlorobenzene is more preferable. These solvents may be used alone, or two or more of them may be used in combination at any ratio.

The amount of the reaction solvent used here is preferably 0.1 to 100 parts by mass, more preferably 1 to 20 parts by mass to 1 part by mass of a phosphonitrile dichloride. When the amount of the reaction solvent used is less than 0.1 part by mass, the concentration of materials in the reaction system is too high, the reaction solution becomes viscous, efficient agitation is difficult, and the reactivity decreases, which is not preferred. When there is an excess of 100 parts by mass, production cost increases and a larger facility is needed, which is not preferred for economic reasons.

The above-mentioned group (III) of the present invention is further described.

The most significant feature of the group (III) is that a phosphonitrile dichloride prepared from a phosphorus chloride and ammonium chloride in a halogenated aromatic hydrocarbon solvent in the presence of a catalyst for the first step reaction is fed to the second step reaction with a phenolic compound and/or an alcohol compound, without isolating the phosphonitrile dichloride from the reaction slurry.

Herein below group (III) is described in detail. The first step reaction in group (III) is described first.

A reaction solvent used in the first step reaction in group (III), i.e., reaction solvent used in preparing a phosphonitrile dichloride from a phosphorus chloride and ammonium chloride is preferably a halogenated aromatic hydrocarbon. The halogenated aromatic hydrocarbon includes monobromobenzene, monochlorobenzene, monofluorobenzene, 1,2-dibromobenzene, 1,3-dibromobenzene, 1,4-dibromobenzene, 1,2-dichlorobenzene, 1,3-dichlorobenzene, 1,4-dichlorobenzene, 1,2-difluorobenzene, 1,3-difluorobenzene, 1,4-difluorobenzene, 2-bromochlorobenzene, 3-bromochlorobenzene, 4-bromochlorobenzene, 2-fluorochlorobenzene, 3-fluorochlorobenzene, 4-fluorochlorobenzene, 2-fluorobromobenzene, 3-fluorobromobenzene, 4-fluorobromobenzene, 1,2,3-tribromobenzene, 1,2,4-tribromobenzene, 1,2,5-tribromobenzene, 1,2,3-trichlorobenzene, 1,2,4-trichlorobenzene, 1,2,5-trichlorobenzene, 1,2,3-trifluorobenzene, 1,2,4-trifluorobenzene, 1,2,5-trifluorobenzene, dibromochlorobenzene, dibromofluorobenzene, dichlorobromobenzene, dichlorofluorobenzene, difluorobromobenzene and difluorochlorobenzene. Among these, monochlorobenzene, 1,2-dichlorobenzene, 1,3-dichlorobenzene, 1,4-dichlorobenzene, 1,2,3-trichlorobenzene, 1,2,4-trichlorobenzene, 1,2,5-trichlorobenzene are preferred, and 1,2-dichlorobenzene, 1,3-dichlorobenzene, 1,4-dichlorobenzene are more preferred. These halogenated aromatic hydrocarbons may be used alone, or two or more of them may be used in combination at any ratio.

The amount of the reaction solvent used here is preferably 0.1 to 100 parts by mass, more preferably 1 to 20 parts by mass to 1 part by mass of a phosphonitrile dichloride. When the amount of the reaction solvent used is less than 0.1 part by mass, the concentration of materials in the reaction system is too high, the agitation efficiency is lowered, and the amount of generated cyclic polymers or linear compounds may increase. When the amount of the reaction solvent used is in excess of 100 parts by mass, production cost increases and a larger facility may be needed.

In group (III), the first step reaction is conducted in the presence of a catalyst. The compound used as a catalyst is a metal oxide or a metal chloride. The metal, for example, includes Mg, Ca, Sr, Ba, Sc, Y, Ti, Zr, V, Nb, Cr, Mo, Mn, Fe, Ru, Co, Rh, Ir, Ni, Pd, Pt, Cu, Ag, Au, Zn, Cd, Hg, Al, Ga, In, Tl, Si, Ge, Sn, Pb, La, Ce, Pr, Nd, Pm, Sm, Eu, Gd, Tb, Dy, Ho, Er, Tm, Yb, Lu. Among these, Mg, Cr, Mn, Fe, Co, Ni, Cu, Zn, Cd, Al, Ga, In, Si, La, Ce, Pr, Nd, Sm, Gd, Dy, Ho, Er and Yb are preferred. Furthermore, among these, zinc oxide, magnesium oxide, aluminum oxide, cobalt oxide, copper oxide, zinc chloride, magnesium chloride, aluminum chloride, cobalt chloride, copper chloride, and zinc chloride are preferable. Zinc oxide and zinc chloride are particularly preferred. These catalysts may be used alone respectively or two or more of them may be used in combination at any ratio.

The amount of the catalyst used is preferably $10^{-5}$ to 1 mol, more preferably $10^{-3}$ to $10^{-1}$ mol per mol of a phosphorus chloride. When the amount of the catalyst used is less than $10^{-5}$ mol, the reaction is not completed or a long time is needed until the reaction is completed. When it is more than 1 mol, there may be no improvement in yield and the effect of increasing the amount of the catalyst used may not be obtained.

In addition to the above described metal oxide or metal chloride, conventionally used catalysts can be used in the first step reaction in group (III). Examples include metal sulfides such as ZnS, metal hydroxides such as $Mg(OH)_2$ and $Al(OH)_3$, metal salts of organic carboxylic acid such as $Ba(CH_3COO)_2$, $Zn(CH_3(CH_2)_{16}COO)_2$, metal salts of perfluoroalkane sulfonic acid such as $Mg(CF_3SO_3)_2$, $Zn(CF_3SO_3)_2$, stratified silicates such as smectite, kaolin, mica, talc and wollastonite.

Pyridine and/or quinoline and/or derivatives thereof can be used together in addition to the above described catalyst as a conventionally known method. The pyridine derivative includes 2-hydroxypyridine, 3-hydroxypyridine, 4-hydroxypyridine, 2,6-dihydroxypyridine, 3-hydroxy-6-methylpyridine, 2-chloropyridine, 3-chloropyridine, 2,6-dichloropyridine, α-picoline, β-picoline, γ-picoline, lutidine, methylethylpyridine. The quinoline derivative includes 2-methylquinoline, 3-methylquinoline, 4-methylquinoline, 5-methylquinoline, 6-methylquinoline, 7-methylquinoline, 8-methylquinoline, 2-chloroquinoline, 3-chloroquinoline, 4-chloroquinone, 5-chloroquinoline, 6-chloroquinoline, 2,3-dichloroquinoline, 2-methyl-4-bromoquinoline, 3-chloroisoquinoline, 8-chloroisoquinoline. These may be used alone or two or more of them may be used in combination at any rate. Although there is no restriction in the amount used of the pyridine and/or the quinoline and/or these derivatives, it is preferred to use a ratio of $10^{-2}$ to 1 mol of this material to 1 mol of a phosphorus chloride.

In the first step reaction in group (III), in order to prepare a phosphonitrile dichloride in a good yield, it is preferred to control the amount of moisture in the reaction system. The amount of moisture in the reaction system is preferably $5 \times 10^{-3}$ mol or less, more preferably $1 \times 10^{-3}$ mol or less to 1 mol of a phosphorus chloride. The amount of moisture in the reaction system of the first step reaction as used herein means the amount of moisture contained in the reaction solution when the reaction starts, and refers to the total amount of moisture contained in the reaction solution including moisture contained in the materials, catalyst, solvent, gas inert to the reaction and moisture adhered to the inside of the reaction equipment.

There is no particular limitation in the method for controlling the amount of moisture in the reaction system. For example, for removing the moisture in the solvent, a dehydrating agent which won't react with the solvent, for example, molecular sieves, a calcium hydride, a metal sodium, a diphosphorus pentoxide, and a calcium chloride may be used. If necessary, distillation can also be performed. For removing the moisture adsorbed on ammonium chloride, a method of drying at 50 to 150° C. under normal pressure or reduced pressure using a hot air drier or a vacuum drier can be mentioned. For removing the moisture adhered to the reaction equipment, a method of heating the inside of reaction equipment under normal pressure or reduced pressure, a method of circulating dried gas at normal temperature or under heating etc. can be mentioned. In addition, it is preferred to carry out the first step reaction in an inert atmosphere to the reaction such as dry nitrogen and argon.

As for the ammonium chloride used in the first step reaction in group (III), a commercially available product may be used, a commercially available product may also be finely pulverized and the ammonium chloride generated by the reaction of hydrogen chloride and ammonia within the reaction system may be used. However, in order to prepare a phosphonitrile dichloride in a good yield, ammonium chloride having a small particle diameter is preferably used, and the average particle diameter of ammonium chloride is 10 μm or less, preferably 5 μm or less and more preferably 2.5 μm or less. There is no restriction in the pulverization method of ammonium chloride, and for example, ball mill, agitation mill, roller mill, jet mill, etc. can be used.

Ammonium chloride is hygroscopic and the hygroscopicity becomes particularly noticeable when it is finely pulverized, and accordingly, fine pulverization becomes difficult. Alternatively, even if it is pulverized, the particles aggregate again and the effect of fine pulverization is no longer obtained. Therefore, it is preferred to conduct pulverization under a dry atmosphere which does not contain moisture, and it is preferred to store it under dry atmosphere after pulverization. Ammonium chloride is preferably dried sufficiently before pulverization from the point of pulverization property. Although there is no restriction in the drying method, a method of drying at 50 to 150° C. for about 1 to 5 hours can be mentioned, for example using a hot air drier or a vacuum drier. Thus, the finely pulverized ammonium chloride under dry atmosphere is preferably supplied into the reaction system as it is.

It is preferred that the amount of the ammonium chloride used is an excessive amount compared to the amount of phosphorus chloride, and it is preferably 1.0 to 2.0 mol, more preferably 1.05 to 1.5 mol to 1 mol of a phosphorus chloride.

As for the phosphorus chloride used in the first step reaction in group (III), phosphorus pentachloride may be used as it is, or a phosphorus chloride obtained by reacting phosphorus trichloride and chlorine, white phosphorus and chlorine, or yellow phosphorus and chlorine prior to the reaction or within the reaction system may be used. Among these, phosphorus pentachloride and a phosphorus chloride obtained by reacting phosphorus trichloride and chlorine is preferred.

As long as the first step reaction in group (III) fulfills the above described reaction conditions, it is possible to conduct the reaction by a variety of conventionally known methods without particular restriction. For example, a method of supplying ammonium chloride and a catalyst into a halogenated aromatic hydrocarbon solvent and dropping this into a solution of phosphorus pentachloride in a halogenated aromatic hydrocarbon while heating and under agitation, a method of supplying ammonium chloride and a catalyst into a reaction solvent and feeding to this solution both phosphorus trichloride and chlorine or both white phosphorus and chlorine can be used while heating and under agitation.

Although there is no particular limitation in the reaction temperature of the first step reaction in group (III), it is preferably in the range of 100 to 200° C., and more preferably 120 to 180° C. When the reaction temperature is less than 100° C., the reaction may not proceed or it may take a long time until the reaction is completed. In the meantime, when the temperature exceeds 200° C., sublimation of a phosphorus chloride may increase and the yield of the phosphonitrile dichloride oligomer may decrease.

In the first step reaction in group (III), an inert gas such as nitrogen may be circulated for the purpose of removing generated hydrogen chloride gas from the reaction system, or the pressure of the inside of the system may be reduced by a vacuum pump or an aspirator.

The progress of the first step reaction can be confirmed by monitoring the amount of the hydrogen chloride gas generated by the reaction of a phosphorus chloride and ammonium chloride. The completion of the reaction may be indicated by the time when the generation of hydrogen chloride gas stops. If the reaction is not complete, agitation may be continued in order to further complete the reaction and perform the aging.

Next, the second step reaction in group (III) is described.

The second step reaction, i.e., reaction of a phosphonitrile dichloride and a phenolic compound and/or an alcohol compound is carried out by reacting a phenolic compound and/or an alcohol compound with a phosphonitrile dichloride prepared by the first step reaction without isolating the phosphonitrile dichloride from the reaction slurry of the first step reaction.

In group (III), a phosphonitrile dichloride prepared by the first step reaction is not isolated and purified from the first step reaction slurry.

Here,

[1] an operation only separating the reaction slurry into solid and liquid such as filtration, centrifugal separation and decantation under warming, at normal temperature or under cooling; and

[2] an operation distilling off the solvent from the reaction slurry and concentrating or drying after the first step reaction is completed:

shall not fall within the category of isolation and purification of a phosphonitrile dichloride.

The reaction mixture of the first step reaction which contains a phosphonitrile dichloride as the main ingredient and is used in the second step reaction in group (III) preferably contains a metal derived from the catalyst for the first step reaction used at the first step reaction in an amount of $1 \times 10^{-6}$ mol or more, preferably $1 \times 10^{-5}$ mol or more, more preferably $1 \times 10^{-4}$ mol or more per mol of the phosphonitrile dichloride. When the metal derived from the catalyst for the first step reaction is less than $1 \times 10^{-6}$ mol, it takes a long time to complete the reaction in the second step reaction, which is not preferred. Furthermore, the phosphonitrile dichloride may be cyclic or linear, and there is no particularly limitation in the composition, i.e., ratio of the cyclic trimer in which m is 3, the cyclic tetramer in which m is 4, the cyclic polymer in which m≧5 in the above described general formula (1), and the linear compounds, and a mixture which contained each ingredient at any ratio can be used.

The solvent used at the second step reaction in the constitution (III) is preferably toluene, ethylbenzene, 1,2-xylene, 1,3-xylene, 1,4-xylene, 1-methyl-2-ethylbenzene, 1-methyl-3-ethylbenzene, 1 methyl-4-ethylbenzene, chloroform, tetrahydrofuran, benzene, dioxane, dimethylformamide, dimethylacetamide, acetonitrile monochlorobenzene, 1,2-dichlorobenzene, 1,3-dichlorobenzene, 1,4-dichlorobenzene, 1,2,3-trichlorobenzene, 1,2,4-trichlorobenzene, 1,2,5-trichlorobenzene. Taking how the operation for carrying out continuously the first step reaction into consideration, monochlorobenzene, 1,2-dichlorobenzene, 1,3-dichlorobenzene, 1,4-dichlorobenzene, 1,2,3-trichlorobenzene, 1,2,4-trichlorobenzene, 1,2,5-trichlorobenzene are still more preferable. Particularly from the viewpoint of shortening the time to the completion of the phenoxylation or alkoxylation reaction, 1,2-dichlorobenzene, 1,3-dichlorobenzene, 1,4-dichlorobenzene are preferred.

The amount of the reaction solvent used is preferably 0.1 to 100 parts by weight, more preferably 1 to 20 parts by weight to 1 part by weight of the phosphonitrile dichloride in terms of the total amount with the reaction solution after the completion of the above described first step reaction. When the amount of the reaction solvent used is less than 0.1 part by weight, the concentration of materials in the reaction system is too high, the reaction solution becomes viscous, efficient agitation is difficult, and the reactivity decreases, which is not preferred. When there is an excess of 100 weight parts, production cost increases and a larger facility is needed, which is not economically preferred.

Moreover, as the phenolic compound represented by the above described general formula (2) or (3) and the alcohol compound represented by the general formula (4) used in group (III), the compounds as illustrated in the above-mentioned groups (I) and (II) can be used.

It is preferred to use an alkaline metal arylate or an alkaline metal alcoholate from the viewpoint of reactivity at the time of reacting a phosphonitrile dichloride and a phenolic compound and/or an alcohol compound like groups (I) and (II) to prepare a phosphonitrilic acid ester. They can be prepared in the similar operations as in groups (I) and (II).

In the second step reaction of groups (I) to (III), it is preferred to control the amount of moisture which exists in the reaction system. The amount of moisture permitted in the reaction system is 0.2 mol or less, preferably 0.1 mol or less and more preferably 0.05 mol or less per mol of a phosphonitrile dichloride. When the amount of moisture in the reaction system is less than 0.2 mol per mol of a phosphonitrile dichloride, the reaction temperature is not decreased due to azeotropy of water and the reaction solvent and reactivity does not drop, hydrolysis of the phosphonitrile dichloride is suppressed, and, as a result, generation of a monohydroxy compound is suppressed.

The amount of moisture in the reaction system herein means the amount of moisture contained in the reaction solution in preparing a phosphonitrile dichloride and a phenolic compound and/or an alcohol compound, and refers to the total amount of the moisture contained in the materials and catalyst, solvent, gas inert to the reaction, and the moisture adhered to the inside of the reaction equipment. Furthermore, the amount of moisture in the reaction system herein includes the water generated in the preparation of an alkaline metal alcoholate and an alkaline metal arylate by reacting an alcohol or a phenol compound with an alkaline metal hydroxide to prepare alkaline metal alcoholate and alkaline metal arylate in starting an alkoxylation reaction or an aryloxylated reaction. In the present invention, removal of the moisture generated during the preparation of an alkaline metal alcoholate and an alkaline metal arylated is important. As for the water generated, it is preferred to control the amount of moisture remaining in the reaction system by removing the generated water out of the reaction system by azeotropy with the reaction solvent etc.

The second step reaction of a phosphonitrile dichloride and a phenolic compound and/or an alcohol compound in groups (I) to (III) can be carried out by various conventionally known methods. For example, a reaction solvent having dissolved therein a phosphonitrile dichloride can be added and reacted to a liquid having dissolved or dispersed therein a phenolic compound and/or an alcohol compound. An alkaline metal hydroxide, a phenolic compound and/or an alcohol compound are made to act in a reaction solvent, water is removed by azeotropic dehydration to prepare a reaction solvent slurry of an alkaline metal arylate and/or an alkaline metal alcoholate, and then a liquid with a dissolved phosphonitrile dichloride in a reaction solvent may be dropped thereto and reacted subsequently. Alternatively, an alkaline metal arylate and/or an alkaline metal alcoholate prepared beforehand are suspended to a reaction solvent, and a liquid having dissolved a phosphonitrile dichloride in a reaction solvent may be dropped thereto and reacted. Or it can be made to react by dropping the above-mentioned slurry to a liquid having dissolved a phosphonitrile dichloride in a reaction solvent.

Although the reaction temperature of the second step reaction is not particularly restricted, it is preferred that the range is 50 to 200° C., more preferably 120 to 185° C. When the reaction temperature is lower than 50° C., it is not preferable because the reaction does not proceed or requires a long time for completing the reaction. In the meantime, hydrolysis becomes noticeable or sublimation takes place if the temperature excesses 200° C., which is not preferred.

The phenolic compound used in the method for preparing a phosphonitrilic acid ester of the present invention may be oxidized by oxygen in air and may generate a coloring ingredient. Therefore, it is preferable to conduct the second step reaction under inert atmosphere such as nitrogen and argon, or under an atmosphere of air.

In the present invention, there is no particular limitation in the method of collecting the generated phosphonitrilic acid ester after the reaction ends, and to washing or purification. For example, the reaction solution is washed with distilled water, and after removing the salt generated at the time of the reaction, the reaction solvent is evaporated and a phosphonitrilic acid ester can be collected. Another example is after washing the reaction solution with an alkaline water and carrying out reduced pressure distillation to remove an excessive amount of a phenolic compound and an alcohol compound, it may be washed with water and a phosphonitrilic acid ester may be collected. Furthermore, the collected reaction product can be recrystalized and purified from a suitable solvent. Moreover, a phosphonitrilic acid ester of a desired composition can be obtained by selecting the solvent at the time of recrystalization purification.

EXAMPLES 1 TO 18, COMPARATIVE EXAMPLES 1 TO 10

Although the present invention is described in more detail below by way of Examples and Comparative Examples, the present invention is not limited to the Examples described.

In the Examples and the Comparative Examples, a composition of cyclic chlorophosphazene oligomers was determined in Gel Permiation Chlomotograph (hereinafter abbreviated as GPC) measurement by internal standard method. When the sum total of the content ratio of cyclic oligomers does not amount to 100% in the results of GPC analysis, the omitted ingredients are those derived from an unreacted phosphorus chloride and linear compounds. The terminal point of aryloxylation and/or alkoxylation reaction was judged from high performance liquid chromatography (hereinafter abbreviated as HPLC.) A composition of a phosphonitrilic acid ester, i.e., ratio of completed products of aryloxylation and/or alkoxylation, monochloro compound and monohydroxy compound were determined from the ratio of the peak areas obtained from $^{31}$P-NMR.

Conditions for measurement of physical properties and preparation method of reaction materials are described below.

<GPC Measurement Condition>
Equipment: HLC-8220 GPC by Tosoh Corp.
Column: TSKgel Super 1000×2
TSKgel Super 2000×2
TSKgel Super 3000×1
TSKguard column Super H-L (by Tosoh Corp.)
Column temperature: 40° C.
Eluant: chloroform
Eluant flow rate: 0.5 ml/min
Internal standard: toluene <HPLC Measurement Condition>
Equipment: HPLC 8020 by Tosoh Corp.
Column: Waters Symmetry 300 C18 5 μm 4.9×150 mm×2
Detection wavelength: 254 nm
Column temperature: 40° C.
Eluant: acetonitrile/water=80/20
Eluant flow rate: 1.0 ml/min A commercial specialty product (Wako Pure Chemical Industries, Ltd.) was used as the solvent for Examples and the Comparative Examples after dried with molecular sieve and diphosphorus pentoxide and distilled. The amount of moisture in the reaction system was measured using a Carl Fischer moisture analysis meter with evaporation equipment.

<Measurement of Moisture Amount>
Equipment: equipment for measuring small amount of moisture CA-100 type by Mitsubishi Kasei Corp. (moisture evaporation equipment: VA-100 type by Mitsubishi Chemical Inc.)
Measuring method: moisture evaporation-coulometric titration method (a sample is placed on a sample boat and put in VA-100 heated at 120° C. and moisture evaporated by nitrogen flow at 300 ml/min was introduced into a titration cell, and the amount of moisture was measured.)
Reagent: Aquamicron AX/CXU (Mitsubishi Kasei Corp.)
Parameter: End Sense 0.1 and Delay (VA) 2

<Yield of Phosphonitrilic Acid Ester>
Yield of a phosphonitrilic acid ester of Examples and Comparative Examples of the present invention is defined as yield of the phosphonitrilic acid ester on the basis of a phosphonitrile dichloride as the material. More specifically, it is computed from (the number of mol of a phosphonitrilic acid ester collected after the reaction)/(the number of mo of a phosphonitrile dichloride supplied before the reaction)×100. The recovery rate is judged to be good when the yield of a phosphonitrilic acid ester is 98% or more.

<Synthesis of Phosphonitrile Dichloride>
38.6 g (0.72 mol) of ammonium chloride having an average particle diameter of 2.1 μm, 0.82 g (10 mmol) of zinc oxide as a catalyst, and 340 g of o-dichlorobenzene were placed in a 1000 ml four-necked flask equipped with a stirring apparatus, a condenser tube, and a dropping funnel and a thermometer, and subjected to nitrogen flow. When a portion of the reaction solution was extracted with a microsyringe and the amount of moisture was measured, it was $2.5 \times 10^{-4}$ mol to 1 mol of phosphorus pentachloride.

Then, a solution having dissolved 125 g (0.6 mol) of phosphorus pentachloride in 340 g of o-dichlorobenzene was dripped using a funnel heated at 105° C. into the reaction system over 241 minutes while the solution was heated in an oil bath temperature of 177° C. The supply rate of phosphorus pentachloride into the reaction system at this time was 0.15 mol/hr to 1 mol of ammonium chloride.

The reaction was continued for 2 hours after the dripping ended. The amount of moisture in the reaction system during the reaction did not exceed $2.5 \times 10^{-4}$ mol to 1 mol of phosphorus pentachloride. Insoluble component (solid component 1) including unreacted ammonium chloride and a catalyst was removed by filtration separation after the reaction ended, and the reaction solvent was evaporated under reduced pressure and the solution was concentrated. 1000 g of petroleum ether was added to a slightly yellow-tinted viscous liquid concentrated by evaporation of the solvent, and insoluble component (solid component 2) was removed by filtration separation. From the collected filtrate, the solvent was evaporated under reduced pressure and the solution was dried, and 69.2 g (yield 99.5% to phosphorus pentachloride) of slightly yellow-tinted solid was obtained. The composition of the reaction product was cyclic trimer: 85.4%, tetramer: 12.3% and >cyclic pentamer: 2.3% according to GPC measurement. The solid component 1 is referred to as filtration residue in Examples 12 to 15.

<Recrystalization Purification of Phosphonitrile Dichloride>

30 g of the phosphonitrile dichloride synthesized in the section of the above <Synthesis of phosphonitrile dichloride> and 200 ml of toluene were put into a 500 ml eggplant type flask and refluxed and dissolved in an oil bath temperature of 110° C. The mixture was slowly cooled to room temperature and then allowed to stand still at −10° C. for 4 hours. The deposited crystal was filtered and the crystal was washed with 50 ml of toluene cooled at −10° C. The crystal was dried with a vacuum dryer at 60° C. The collected crystal was 21.8 g (yield: 72.7%). The composition of the collected crystal was trimer: 99.5% and tetramer: 0.5% according to GPC measurement.

<Preparation of $(NH_4)_3ZnCl_5$>

5.0 g (0.037 mol) of zinc chloride and 5.9 g (0.110 mol) of ammonium chloride were put into a 50 ml eggplant type flask, and 50 ml of distilled water was added. Reflux heating was performed at 110° C. in an oil bath for 1 hour. Water was removed by rotary evaporator after the mixture was allowed to cool to room temperature, and it was dried with a vacuum dryer at 110° C. for 5 hours. Consequently, 10.7 g of white powder was obtained.

<Preparation of $NH_4MgCl_3$>

5.0 g (0.052 mol) of magnesium chloride and 2.8 g (0.052 mol) of ammonium chloride were put into a 50 ml eggplant type flask, and 50 ml of distilled water was added thereto. Reflux heating was performed at 110° C. in an oil bath for 1 hour. Water was removed by rotary evaporator after the mixture was allowed to cool to room temperature, and it was dried with a vacuum dryer at 110° C. for 5 hours. Consequently, 7.5 g of white powder was obtained.

<Preparation of $(NH_4)_2CoCl_4$>

6.8 g (0.052 mol) of cobalt chloride and 5.6 g (0.104 mol) of ammonium chloride were put into a 50 ml eggplant type flask, and 50 ml of distilled water was added thereto. Reflux heating was performed at 110° C. in an oil bath for 1 hour. Water was removed by rotary evaporator after the mixture was allowed to cool to room temperature, and it was dried with a vacuum dryer at 110° C. for 5 hours. Consequently, 12.3 g of white powder were obtained.

<Preparation of $(NH_4)_2CuCl_4$>

7.0 g (0.052 mol) of copper chloride and 5.6 g (0.104 mol) of ammonium chloride were put into a 50 ml eggplant type flask, and 50 ml of distilled water was added thereto. Reflux heating was performed at 110° C. in an oil bath for 1 hour. Water was removed by rotary evaporator after the mixture was allowed to cool to room temperature, and it was dried with a vacuum dryer at 110° C. for 5 hours. Consequently, 12.5 g of white powder was obtained.

EXAMPLE 1

7.05 g (0.075 mol) of phenol, 4.20 g (0.075 mol) of potassium hydroxide and 20 g of xylene were put into a 200 ml four-necked flask equipped with a stirring apparatus, a condenser tube, a dropping funnel and a thermometer, and potassium phenoxide was prepared under nitrogen flow, while carrying out azeotropic dehydration at an oil bath temperature of 150° C. After the mixture was allowed to cool to room temperature, 0.015 g (0.05 mmol) of the prepared $(NH_4)_3ZnCl_5$ was added thereto and 3.63 g (0.031 mol) of the phosphonitrile dichloride subjected recrystalization purification and dissolved in 20 g of xylene was dripped over 15 minutes. A portion of the reaction solution was extracted with a microsyringe and the amount of moisture was measured, and the result was 0.010 mol per mol of the phosphonitrile dichloride. Then, it was heated in an oil bath temperature of 150° C. The reaction was followed by HPLC, and the reaction was ended in 2 hours after the inside of the reaction system reached refluxing state. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.07 g (98.7% of yield converted from the phosphonitrile dichloride) of reaction product was obtained. Results of $^{31}$P-NMR measurement are shown in Table 1.

EXAMPLE 2

7.05 g (0.075 mol) of phenol, 4.20 g (0.075 mol) of potassium hydroxide and 25 g of monochlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 140° C. After the mixture was allowed to cool to room temperature, 0.015 g (0.05 mmol) of the prepared $(NH_4)_3ZnCl_5$ was added thereto and 3.63 g (0.031 mol) of the phosphonitrile dichloride subjected recrystalization purification and dissolved in 25 g of monochlorobenzene was dripped over 15 minutes. A portion of the reaction solution was extracted with a microsyringe and the amount of moisture was measured, and the result was 0.012 mol per mol of the phosphonitrile dichloride. Then, it was heated in an oil bath temperature of 140° C. The reaction was followed by HPLC, and the reaction was ended in 2.5 hours after the inside of the reaction system reached refluxing state. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.05 g (98.4% of yield converted from the phosphonitrile dichloride) of the reaction product was obtained. Results of $^{31}$P-NMR measurement are shown in Table 1.

EXAMPLE 3

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.015 g (0.05 mmol) of the prepared $(NH_4)_3ZnCl_5$ was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.015 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.06 g (98.5% of yield converted from the phosphonitrile dichloride) of the reaction product was obtained. Results of $^{31}$P-NMR measurement are shown in Table 1.

EXAMPLE 4

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.007 g (0.05 mmol) of the prepared $NH_4MgCl_3$ was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.014 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.03 g (98.2% of yield converted from the phosphonitrile dichloride) of the reaction product was obtained. Results of $^{31}$P-NMR measurement are shown in Table 1.

EXAMPLE 5

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration at an oil bath temperature of 190° C. After the mixture was allowed to cool to room temperature, 0.007 g (0.05 mmol) of $ZnCl_2$ was added thereto and 3.63 g (0.031 mol) of the phosphonitrile dichloride was subjected recrystalization purification and dissolved in 25 g of 1,2-dichlorobenzene was dripped over 15 minutes. A portion of the reaction solution was extracted with a microsyringe and the amount of moisture was measured, and the result was 0.017 mol per mol of the phosphonitrile dichloride. Then, it was heated in an oil bath temperature of 150° C. The reaction was followed by HPLC, and the reaction was ended in 2.0 hours after the inside of the reaction system reached 140° C. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.06 g (98.6% of yield converted from the phosphonitrile dichloride) of the reaction product was obtained. Results of $^{31}$P-NMR measurement are shown in Table 1.

EXAMPLE 6

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.005 g (0.05 mmol) of $MgCl_2$ was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.019 mol per mol of the phosphonitrile dichloride. Then, it was heated in an oil bath temperature of 150° C. The reaction was followed by HPLC, and the reaction was ended in 2.0 hours after the inside of the reaction system reached 140° C. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.03 g (98.1% of yield converted from the phosphonitrile dichloride) of the reaction product was obtained. Results of $^{31}$P-NMR measurement are shown in Table 1.

EXAMPLE 7

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.007 g (0.05 mmol) of $CoCl_2$ was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.018 mol per mol of the phosphonitrile dichloride. Then, it was heated in an oil bath temperature of 150° C. The reaction was followed by HPLC, and the reaction was ended in 2.0 hours after the inside of the reaction system reached 140° C. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.04 g (98.3% of yield converted from the phosphonitrile dichloride) of the reaction product was obtained. Results of $^{31}$P-NMR measurement are shown in Table 1.

EXAMPLE 8

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.012 g (0.05 mmol) of the prepared $(NH_4)_2CoCl_4$ was added thereto and 3.63 g (0.031 mol) of the phosphonitrile dichloride subjected recrystalization purification and dissolved in 25 g of 1,2-dichlorobenzene was dropped over 15 minutes. A portion of the reaction solution was extracted with a microsyringe and the amount of moisture was measured, and the result was 0.016 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.07 g (98.7% of yield converted from the phosphonitrile dichloride) of the reaction product was obtained. Results of $^{31}P$-NMR measurement are shown in Table 1.

EXAMPLE 9

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.005 g (0.05 mmol) of CuCl was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.012 mol per mol of the phosphonitrile dichloride. Then, it was heated in an oil bath temperature of 150° C. The reaction was followed by HPLC, and the reaction was ended in 2.0 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.03 g (98.2% of yield converted from the phosphonitrile dichloride) of the reaction product was obtained. Results of $^{31}P$-NMR measurement are shown in Table 1.

EXAMPLE 10

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.012 g (0.05 mmol) of the prepared $(NH_4)_2CuCl_4$ was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.013 mol per mol of the phosphonitrile dichloride. Then, it was heated at an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.05 g (98.4% of yield converted from the phosphonitrile dichloride) of the reaction product was obtained. Results of $^{31}P$-NMR measurement are shown in Table 1.

EXAMPLE 11

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 0.015 g (0.05 mmol) of the prepared $(NH_4)_3ZnCl_5$ was added thereto and 3.63 g (0.031 mol) of the phosphonitrile dichloride subjected recrystalization purification and dissolved in 25 g of 1,2-dichlorobenzene was dropped over 15 minutes. A portion of the reaction solution was extracted with a microsyringe and the amount of moisture was measured, and the result was 0.014 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.05 g (98.4% of yield converted from the phosphonitrile dichloride) of the reaction product was obtained. Results of $^{31}P$-NMR measurement are shown in Table 1.

EXAMPLE 12

7.05 g (0.075 mol) of phenol, 4.20 g (0.075 mol) of potassium hydroxide and 20 g of xylene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 150° C. After the mixture was allowed to cool to room temperature, 5.00 mg of filtration residue obtained from the above described section <Synthesis of phosphonitrile dichloride> was added thereto and 3.63 g (0.031 mol) of the phosphonitrile dichloride subjected recrystalization purification and dissolved in 20 g of xylene was dripped over 15 minutes. A portion of the reaction solution was extracted with a microsyringe and the amount of moisture was measured, and the result was 0.009 mol per mol of the phosphonitrile dichloride. Then, it was heated in an oil bath temperature of 150° C. The reaction was followed by HPLC, and the reaction was ended in 2.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.02 g (98.1% of yield converted from the phosphonitrile dichloride) of the reaction product was obtained. Results of $^{31}$P-NMR measurement are shown in Table 1.

EXAMPLE 13

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 5.00 mg of filtration residue obtained from the above described section <Synthesis of phosphonitrile dichloride> was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.010 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.04 g (98.3% of yield converted from the phosphonitrile dichloride) of the reaction product was obtained. Results of $^{31}$P-NMR measurement are shown in Table 1.

EXAMPLE 14

7.05 g (0.075 mol) of phenol, 3.00 g (0.075 mol) of sodium hydroxide and 25 g of 1,2-dichlorobenzene were put into a 200 ml four-necked flask equipped with a stirring apparatus, a condenser tube, a dropping funnel and a thermometer, and sodium phenoxide was prepared under nitrogen flow, while carrying out azeotropic dehydration in an oil bath temperature of 190° C. After the mixture was allowed to cool to room temperature, 5.00 mg of filtration residue obtained from the above described section <Synthesis of phosphonitrile dichloride> was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.021 mol per mol of the phosphonitrile dichloride. Then, it was heated in an oil bath temperature of 150° C. The reaction was followed by HPLC, and the reaction was ended in 2.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.12 g (98.1% of yield converted from the phosphonitrile dichloride) of the reaction product was obtained. Results of 31 P-NMR measurement are shown in Table 1.

EXAMPLE 15

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 5.00 mg of filtration residue obtained from the above described section <Synthesis of phosphonitrile dichloride> was added thereto and 3.63 g (0.031 mol) of the phosphonitrile dichloride subjected recrystalization purification and dissolved in 25 g of 1,2-dichlorobenzene was dripped over 15 minutes. A portion of the reaction solution was extracted with a microsyringe and the amount of moisture was measured, and the result was 0.013 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution 2 times and then neutralized with a dilute hydrochloric acid. After the reaction solution was further washed with 50 ml of distilled water, the reaction solvent was evaporated under reduced pressure. Consequently, 7.05 g (98.5% of yield converted from the phosphonitrile dichloride) of the reaction product was obtained. Results of $^{31}$P-NMR measurement are shown in Table 1.

EXAMPLE 16

7.05 g (0.075 mol) of phenol, 0.17 g (1.27 mmol) of anhydrous aluminum chloride and 25 g of 1,2-dichlorobenzene were put into a 200 ml four-necked flask equipped with a stirring apparatus, a condenser tube, a dropping funnel and a thermometer, and 3.63 g (0.031 mol) of the phosphonitrile dichloride subjected recrystalization purification and dissolved in 25 g of 1,2-dichlorobenzene was dripped over 15 minutes in nitrogen flow while agitated under ice cooling. A portion of the reaction solution was extracted with a microsyringe and the amount of moisture was measured, and the result was 0.008 mol per mol of the phosphonitrile dichloride. Then, it was heated in an oil bath temperature of 170° C. The reaction was followed by HPLC, and the reaction was ended in 5 hours after the inside of the reaction system reached 160° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.02 g (98.0% of yield con-

EXAMPLE 17

<First Step Reaction>

1.93 g (0.036 mol) of ammonium chloride having an average particle diameter of 2.1 μm, 0.041 g (0.5 mmol) of zinc oxide and 17 g of 1,2-dichlorobenzene were put into a 100 ml four-necked flask equipped with a stirring apparatus, a condenser tube, a dropping funnel and a thermometer, and subjected to nitrogen flow. A portion of the reaction solution was extracted with a microsyringe and the amount of moisture was measured, and the result was $3.2 \times 10^{-4}$ mol per mol of phosphorus pentachloride. Then, a solution having dissolved 6.25 g (0.03 mol) of phosphorus pentachloride in 17 g of 1,2-dichlorobenzene was dripped using a funnel heated at 105° C. into the reaction system while the solution was heated in an oil bath temperature of 177° C. The reaction was continued for two hours after the dripping ended. The amount of moisture in the reaction system during the reaction did not exceed $3.2 \times 10^{-4}$ mol to 1 mol of phosphorus pentachloride. The reaction solution was used for the second step reaction without subjected to filtration.

<Second Step Reaction>

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, the first step reaction solution was dripped over 15 minutes. A portion of the reaction solution was extracted with a microsyringe and the amount of moisture was measured, and the result was 0.015 mol per mol of the phosphonitrile dichloride. Then, it was heated in an oil bath temperature of 150° C. The reaction was followed by HPLC, and the reaction was ended in 1.5 hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 6.77 g (98.4% of yield converted from the phosphonitrile dichloride) of the reaction product was obtained. Results of $^{31}$P-NMR measurement are shown in Table 1.

EXAMPLE 18

<First Step Reaction>

1.93 g (0.036 mol) of ammonium chloride having an average particle diameter of 2.1 μm, 0.041 g (0.5 mmol) of zinc oxide and 17 g of 1,2-dichlorobenzene were put into a 100 ml four-necked flask equipped with a stirring apparatus, a condenser tube, a dropping funnel and a thermometer, and subjected to nitrogen flow. A portion of the reaction solution was extracted with a microsyringe and the amount of moisture was measured, and the result was $2.5 \times 10^{-4}$ mol per mol of phosphorus pentachloride. Then, a solution having dissolved 6.25 g (0.03 mol) of phosphorus pentachloride in 17 g of 1,2-dichlorobenzene was dripped using a funnel heated at 105° C. into the reaction system while the solution was heated in an oil bath temperature of 177° C. The reaction was continued for two hours after the dropping ended. The amount of moisture in the reaction system during the reaction did not exceed $2.5 \times 10^{-4}$ mol to 1 mol of phosphorus pentachloride. It was allowed to cool to room temperature after the reaction ended, and unreacted ammonium chloride was removed by filtration under reduced pressure. The amount of zinc contained in the filtrate was $2.4 \times 10^{-4}$ mol per mol of the phosphonitrile dichloride.

<Second Step Reaction>

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration at an oil bath temperature of 190° C. After the mixture was allowed to cool to room temperature, the first step reaction solution was dripped over 15 minutes. A portion of the reaction solution was extracted with a microsyringe and the amount of moisture was measured, and the result was 0.021 mol per mol of the phosphonitrile dichloride. Then, it was heated in an oil bath temperature of 150° C. The reaction was followed by HPLC, and the reaction was ended in two hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 6.80 g (98.2% of yield converted from the phosphonitrile dichloride) of the reaction product was obtained. Results of $^{31}$P-NMR measurement are shown in Table 1.

COMPARATIVE EXAMPLE 1

7.05 g (0.075 mol) of phenol and 25 g of 1,2-dichlorobenzene were put into a 200 ml four-necked flask equipped with a stirring apparatus, a condenser tube, a dropping funnel and a thermometer, and 3.63 g (0.031 mol) of the phosphonitrile dichloride subjected recrystalization purification and dissolved in 25 g of 1,2-dichlorobenzene was dripped over 15 minutes in nitrogen flow while agitated under ice cooling. A portion of the reaction solution was extracted with a microsyringe and the amount of moisture was measured, and the result was 0.012 mol per mol of the phosphonitrile dichloride. Then, it was heated in an oil bath temperature of 170° C. The reaction was followed by HPLC, and the reaction was ended in 12 hours after the inside of the reaction system reached 160° C., but a monochloro compound remained according to the results by HPLC. The reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 6.59 g (92.1% of yield converted from the chlorophosphazene) of the reaction product was obtained. Results of $^{31}$P-NMR measurement are shown in Table 2.

COMPARATIVE EXAMPLE 2

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, 3.63 g (0.031 mol) of the phosphonitrile dichloride obtained from the above described section <Synthesis of phosphonitrile dichloride> and dissolved in 25 g of 1,2-dichlorobenzene was dripped over 15 minutes. A portion of the reaction solution was extracted with a microsyringe and the amount of moisture was measured, and the result was 0.017 mol per mol of the phosphonitrile dichloride. Then, it was heated in an oil bath temperature of 150° C. The reaction was followed by HPLC, and the reaction was ended in five hours after the inside of the reaction system reached 140° C. After the reaction ended, the reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 7.11 g (97.9% of yield converted from the phosphonitrile dichloride) of the reaction product was obtained. Results of $^{31}$P-NMR measurement are shown in Table 2.

COMPARATIVE EXAMPLE 3

5.11 g (0.054 mol) of phenol, 3.00 g (0.054 mol) of potassium hydroxide and 15 g of xylene were put into a 100 ml four-necked flask equipped with a stirring apparatus, a condenser tube, a dropping funnel, a thermometer and a Dean Stark trap, and potassium phenoxide was prepared under nitrogen flow, while carrying out azeotropic dehydration in an oil bath temperature of 150° C. After the mixture was allowed to cool to room temperature, 2.50 g (0.022 mol) of the phosphonitrile dichloride subjected recrystalization purification and dissolved in 15 g of xylene was dropped over 10 minutes under agitation. A portion of the reaction solution was extracted with a microsyringe and the amount of moisture was measured, and the result was 0.021 mol per mol of the phosphonitrile dichloride. Then, reflux heating was performed in an oil bath temperature of 150° C. At this time, the temperature in the reaction system was 141° C. The reaction was followed by HPLC, and the reaction was ended in 12 hours after the start of reflux, but a monochloro compound remained according to the results by HPLC. The reaction solution was washed with 50 ml of 10% potassium hydroxide aqueous solution two times and then neutralized with a dilute hydrochloric acid. After the reaction solution was further washed with 50 ml of distilled water, the reaction solvent was evaporated under reduced pressure. Consequently, 4.76 g (95.2% of yield converted from the chlorophosphazene) of the reaction product was obtained. Results of $^{31}$P-NMR measurement are shown in Table 2.

COMPARATIVE EXAMPLE 4

5.11 g (0.054 mol) of phenol, 3.00 g (0.054 mol) of potassium hydroxide and 18 g of monochlorobenzene were put into a 100 ml four-necked flask equipped with a stirring apparatus, a condenser tube, a dropping funnel, a thermometer and a Dean Stark trap, and potassium phenoxide was prepared under nitrogen flow, while carrying out azeotropic dehydration in an oil bath temperature of 150° C. After the mixture was allowed to cool to room temperature, 2.50 g (0.022 mol) of the phosphonitrile dichloride subjected recrystalization purification and dissolved in 15 g of monochlorobenzene was dripped over 10 minutes under agitation. A portion of the reaction solution was extracted with a microsyringe and the amount of moisture was measured, and the result was 0.016 mol per mol of the phosphonitrile dichloride. Then, reflux heating was performed in an oil bath temperature of 150° C. At this time, the temperature in the reaction system was 131° C. The reaction was followed by HPLC, and the reaction was ended in twelve hours after the start of reflux but a monochloro compound remained according to the results by HPLC. The reaction solution was washed with 50 ml of 10% potassium hydroxide aqueous solution two times and then neutralized with a dilute hydrochloric acid. The reaction solution was further washed with 50 ml of distilled water but separation between oil and water was generally poor. Then the reaction solvent was evaporated under reduced pressure. Consequently, 4.72 g (94.4% of yield converted from the chlorophosphazene) of the reaction product was obtained. Results of $^{31}$P-NMR measurement are shown in Table 2.

COMPARATIVE EXAMPLE 5

5.11 g (0.054 mol) of phenol, 3.00 g (0.054 mol) of potassium hydroxide and 25 g of 1,2-dichlorobenzene were put into a 100 ml four-necked flask equipped with a stirring apparatus, a condenser tube, a dropping funnel, a thermometer and a Dean Stark trap, and potassium phenoxide was prepared under nitrogen flow, while carrying out azeotropic dehydration in an oil bath temperature of 190° C. After the mixture was allowed to cool to room temperature, 2.50 g (0.022 mol) of the phosphonitrile dichloride subjected recrystalization purification and dissolved in 10 g of 1,2-dichlorobenzene was dropped over 10 minutes under agitation. A portion of the reaction solution was extracted with a microsyringe and the amount of moisture was measured, and the result was 0.252 mol per mol of the phosphonitrile dichloride. Then, it was heated and agitated in an oil bath temperature of 150° C. The reaction was followed by HPLC, and the reaction was ended in twelve hours after the inside of the reaction system reached 140° C. but a monochloro compound remained according to the results by HPLC. After the reaction ended, the reaction solution was washed with 50 ml of 10% potassium hydroxide aqueous solution 2 times and then neutralized with a dilute hydrochloric acid. The reaction solution was further washed with 50 ml of distilled water but separation between oil and water was generally poor. Then the reaction solvent was evaporated under reduced pressure. Consequently, 4.74 g (94.8% of yield converted from the chlorophosphazene) of the reaction product was obtained. Results of $^{31}$P-NMR measurement are shown in Table 2.

COMPARATIVE EXAMPLE 6

5.11 g (0.054 mol) of phenol, 0.26 g (1.9 mmol) of zinc chloride and 25 g of dimethylformamide were put into a 100 ml four-necked flask equipped with a stirring apparatus, a condenser tube, a dropping funnel and a thermometer, and 2.50 g (0.022 mol) of the phosphonitrile dichloride subjected recrystalization purification and dissolved in 15 g of dimethylformamide was dripped over 10 minutes under agitation in nitrogen flow. A portion of the reaction solution was extracted with a microsyringe and the amount of moisture was measured, and the result was 0.018 mol per mol of the phosphonitrile dichloride. Then, it was heated and agitated in an oil bath temperature of 80° C. The reaction was followed by HPLC, and the reaction was ended in eight hours after the inside of the reaction system reached 80° C. After the reaction ended, the reaction solution was filtrated and the reaction solvent was evaporated under reduced pressure. Consequently, 4.92 g (98.4% of yield converted from the chlorophosphazene) of the reaction product was obtained. Results of $^{31}$P-NMR measurement are shown in Table 2.

COMPARATIVE EXAMPLE 7

1.25 g (0.054 mol) of metal sodium and 25 g of n-heptane were put into a 100 ml four-necked flask equipped with a stirring apparatus, a condenser tube, a dropping funnel, a thermometer and a Dean Stark trap, and the metal sodium was dissolved in an oil bath temperature of 120° C. Then, 5.11 g (0.054 mol) of phenol dissolved in 25 g of n-heptane was dripped over 10 minutes while removing by-product hydrogen gas and sodium phenoxide was prepared. After the mixture was allowed to cool to room temperature, 2.50 g (0.022 mol) of the phosphonitrile dichloride subjected recrystalization purification and dissolved in 15 g of 1,2-dichlorobenzene was dripped over ten minutes under agitation. A portion of the reaction solution was extracted with a microsyringe and the amount of moisture was measured, and the result was 0.052 mol per mol of the phosphonitrile dichloride. Then, it was heated and agitated in an oil bath temperature of 150° C. The reaction was followed by HPLC, and the reaction was ended in twelve hours after the inside of the reaction system reached reflux state, but a monochloro compound remained according to the results by HPLC. After the reaction ended, the reaction solution was washed with 50 ml of 10% potassium hydroxide aqueous solution two times and then neutralized with a dilute hydrochloric acid. The reaction solution was further washed with 50 ml of distilled water but separation between oil and water was generally poor. Then the reaction solvent was evaporated under reduced pressure. Consequently, 4.66 g (93.2% of yield converted from the phosphonitrile dichloride) of the reaction product was obtained. Results of $^{31}$P-NMR measurement are shown in Table 2.

COMPARATIVE EXAMPLE 8

5.11 g (0.054 mol) of phenol, 3.00 g (0.054 mol) of potassium hydroxide, 1.05 g ($3.25 \times 10^{-3}$ mol) of tetra-n-butyl ammonium bromide and 12 g of distilled water were put into a 100 ml four-necked flask equipped with a stirring apparatus, a condenser tube, a dropping funnel and a thermometer, and 2.50 g (0.022 mol) of the phosphonitrile dichloride subjected recrystalization purification and dissolved in 15 g of 1,2-dichlorobenzene was dripped over 10 minutes under agitation in nitrogen flow. Then, it was heated and agitated in an oil bath temperature of 150° C. The reaction was followed by HPLC, and the reaction was ended in twelve hours after the inside of the reaction system reached reflux state, but a monochloro compound remained according to the results by HPLC. After the reaction ended, the reaction solution was washed with 50 ml of 10% potassium hydroxide aqueous solution two times and then neutralized with a dilute hydrochloric acid. The reaction solution was further washed with 50 ml of distilled water but the separation between oil and water was generally poor. Then the reaction solvent was evaporated under reduced pressure. Consequently, 3.40 g (67.9% of yield converted from the phosphonitrile dichloride) of the reaction product was obtained. Results of $^{31}$P-NMR measurement are shown in Table 2.

COMPARATIVE EXAMPLE 9

5.11 g (0.054 mol) of phenol, 8.22 g (0.081 mol) of triethylamine and 0.35 g (0.003 mol) of 4-trimethylaminopyridine were put into a 100 ml four-necked flask equipped with a stirring apparatus, a condenser tube, a dropping funnel and a thermometer, and 2.50 g (0.022 mol) of the phosphonitrile dichloride subjected recrystalization purification and dissolved in 15 g of 1,2-dichlorobenzene was dripped over 20 minutes in nitrogen flow while agitated under ice cooling. Then, it was agitated in water bath so that the temperature of the reaction system could reach 30° C. The reaction was followed by HPLC, and the reaction was ended in twelve hours after the start of refluxing but a monochloro compound remained according to the results by HPLC. After the reaction ended, the reaction solution was washed with 50 ml of 10% potassium hydroxide aqueous solution two times and then neutralized with a dilute hydrochloric acid. The reaction solution was further washed with 50 ml of distilled water but the separation between oil and water was generally poor. Then the reaction solvent was evaporated under reduced pressure. Consequently, 4.69 g (93.8% of yield converted from the phosphonitrile dichloride) of the reaction product was obtained. Results of $^{31}$P-NMR measurement are shown in Table 2.

COMPARATIVE EXAMPLE 10

<First Step Reaction>

1.93 g (0.036 mol) of ammonium chloride having an average particle diameter of 2.1 μm, 0.041 g (0.5 mmol) of zinc oxide and 17 g of 1,2-dichlorobenzene were put into a 100 ml four-necked flask equipped with a stirring apparatus, a condenser tube, a dropping funnel and a thermometer, and subjected to nitrogen flow. A portion of the reaction solution was extracted with a microsyringe and the amount of moisture was measured, and the result was $1.9 \times 10^{-4}$ mol per mol of the phosphorus pentachloride. Then, a solution having dissolved 6.25 g (0.03 mol) of phosphorus pentachloride in 17 g of 1,2-dichlorobenzene was dripped using a funnel heated at 105° C. into the reaction system while the solution was heated at an oil bath temperature of 177° C. The reaction was continued for two hours after the dropping ended. The amount of moisture in the reaction system during the reaction did not exceed $2.5 \times 10^{-4}$ mol to 1 mol of phosphorus pentachloride. It was allowed to cool to room temperature after the reaction ended, and unreacted ammonium chloride was removed by filtration under reduced pressure and the reaction solution was put into a 100 ml of separation funnel. 50 ml of distilled water was added thereto and the separation funnel was shaken well at room temperature and the funnel was allowed to stand still to separate oil and water. After the dichlorobenzene phase was separated, magnesium sulfate was added thereto and the dichlorobenzene phase was agitated for 30 minutes. Molecular sieve 4A was added thereto after magnesium sulfate was removed by filtration. The molecular sieve was removed by filtration separation after stand-still overnight. The amount of zinc in the filtrate was $5.2 \times 10^{-7}$ mol per mol of the phosphonitrile dichloride.

<Second Step Reaction>

7.05 g (0.075 mol) of phenol, 4.20 g (0.075 mol) of potassium hydroxide and 25 g of 1,2-dichlorobenzene were put into a 200 ml four-necked flask equipped with a stirring apparatus, a condenser tube, a dropping funnel and a thermometer, and potassium phenoxide was prepared under nitrogen flow, while carrying out azeotropic dehydration in an oil bath temperature of 190° C. After the mixture was allowed to cool to room temperature, a dichlorobenzene solution containing the phosphonitrile dichloride synthesized by the first step reaction was dripped over 20 minutes. A portion of the reaction solution was extracted with a microsyringe and the amount of moisture was measured, and the result was 0.025 mol per mol of the phosphonitrile dichloride. Then, it was heated in an oil bath temperature of 150° C. The reaction was followed by HPLC, and the reaction was ended in five hours after the inside of the reaction system reached 140° C. After the reaction ended, the reaction solution was washed with 50 ml of 10% potassium hydroxide aqueous solution two times and then neutralized with a dilute hydrochloric acid. The reaction solution was further washed with 50 ml of distilled water. Consequently, 6.59 g (96.5% of yield converted from the phosphonitrile dichloride) of the reaction product was obtained. Results of $^{31}$P-NMR measurement are shown in Table 2.

TABLE 1

| Example | Solvent | Catalyst | 1) Amount of moisture in the reaction system (mol) | 2) Yield (%) | Reaction time (hrs) | 3) Composition of product (%) Completely substituted compound | Monochloro compound |
|---|---|---|---|---|---|---|---|
| 1 | Xylene | $(NH_4)_3ZnCl_5$ | 0.010 | 98.7 | 2.0 | 100.0 | 0.0 |
| 2 | Monochlorobenzene | $(NH_4)_3ZnCl_5$ | 0.012 | 98.4 | 2.5 | 100.0 | 0.0 |
| 3 | 1,2-Dichlorobenzene | $(NH_4)_3ZnCl_5$ | 0.015 | 98.5 | 1.5 | 100.0 | 0.0 |
| 4 | 1,2-Dichlorobenzene | $NH_4MgCl_3$ | 0.014 | 98.2 | 1.5 | 100.0 | 0.0 |
| 5 | 1,2-Dichlorobenzene | $ZnCl_2$ | 0.017 | 98.6 | 2.0 | 100.0 | 0.0 |
| 6 | 1,2-Dichlorobenzene | $MgCl_2$ | 0.019 | 98.1 | 2.0 | 100.0 | 0.0 |
| 7 | 1,2-Dichlorobenzene | $CoCl_2$ | 0.018 | 98.3 | 2.0 | 100.0 | 0.0 |
| 8 | 1,2-Dichlorobenzene | $(NH_4)_2CoCl_4$ | 0.016 | 98.7 | 1.5 | 100.0 | 0.0 |
| 9 | 1,2-Dichlorobenzene | CuCl | 0.012 | 98.2 | 2.0 | 100.0 | 0.0 |
| 10 | 1,2-Dichlorobenzene | $(NH_4)_2CuCl_4$ | 0.013 | 98.4 | 1.5 | 100.0 | 0.0 |
| 11 | 1,2-Dichlorobenzene | $(NH_4)_3ZnCl_5$ | 0.014 | 98.4 | 1.5 | 100.0 | 0.0 |
| 12 | Xylene | Filtration residue | 0.009 | 98.1 | 2.5 | 100.0 | 0.0 |
| 13 | 1,2-Dichlorobenzene | Filtration residue | 0.010 | 98.3 | 1.5 | 100.0 | 0.0 |
| 14 | 1,2-Dichlorobenzene | Filtration residue | 0.013 | 98.5 | 1.5 | 100.0 | 0.0 |
| 15 | 1,2-Dichlorobenzene | Filtration residue | 0.021 | 98.1 | 2.5 | 100.0 | 0.0 |
| 16 | 1,2-Dichlorobenzene | $AlCl_3$ | 0.008 | 98.0 | 5.0 | 100.0 | 0.0 |
| 17 | 1,2-Dichlorobenzene | Continuous reaction (without filtration) | 0.015 | 98.4 | 1.5 | 100.0 | 0.0 |
| 18 | 1,2-Dichlorobenzene | Continuous reaction (with filtration) | 0.021 | 98.2 | 2.0 | 100.0 | 0.0 |

1) Molar number of water per mol of the phosphonitrile dichloride
2) Yield converted from the phosphonitrile dichloride
3) Determined from the ratio of the peak areas obtained from $^{31}$P-NMR (wherein 0.0% in the composition means that no peak was detected in NMR measurement)

TABLE 2

| Comparative Example | Solvent | Catalyst | 1) Amount of moisture in the reaction system (mol) | 2) Yield (%) | Reaction time (hrs) | 3) Composition of product (%) Completely substituted compound | Monochloro compound |
|---|---|---|---|---|---|---|---|
| 1 | 1,2-Dichlorobenzene | Not added | 0.012 | 92.1 | >12 | 91.3 | 8.7 |
| 2 | 1,2-Dichlorobenzene | Not added | 0.017 | 97.9 | 5 | 99.6 | 0.4 |
| 3 | Xylene | Not added | 0.021 | 95.2 | >12 | 98.3 | 1.7 |
| 4 | Monochlorobenzene | Not added | 0.016 | 94.4 | >12 | 95.2 | 4.8 |
| 5 | 1,2-Dichlorobenzene | Not added | 0.252 | 94.8 | >12 | 91.2 | 8.8 |
| 6 | Dimethylformamide | Zinc chloride | 0.018 | 98.4 | 8 | 99.7 | 0.3 |
| 7 | 1,2-Dichlorobenzene/n-heptane | Not added | 0.052 | 93.2 | >12 | 89.3 | 10.7 |
| 8 | 1,2-Dichlorobenzene | Tetrabutylammonium bromide | Not measured | 67.9 | >12 | 58.8 | 41.2 |
| 9 | 1,2-Dichlorobenzene | 4-Trimethyl-aminopyridine/triethylamine | 0.018 | 93.8 | >12 | 99.5 | 0.5 |
| 10 | 1,2-Dichlorobenzene | Continuous reaction (treatment with water) | 0.025 | 97.4 | 5 | 99.5 | 0.5 |

1) Molar number of water per mol of the phosphonitrile dichloride
2) Yield converted from the phosphonitrile dichloride
3) Determined from the ratio of the peak areas obtained from $^{31}$P-NMR (wherein 0.0% in the composition means that no peak was detected in NMR measurement)

As it is apparent from a comparison between the Examples (Table 1) and the Comparative Examples (Table 2), it turns out that the reaction is completed rapidly and a phosphonitrilic acid ester that does not contain a monochloro compound can be obtained when the catalyst of the present invention is used and the amount of moisture in the reaction system is controlled. Furthermore, it turns out that when the first step reaction solution is fed to the second step reaction, the reaction is completed very rapidly. On the other hand, in the case where a catalyst is not used, even if the amount of moisture in the reaction system is low, it turn out that it takes a long time to complete the reaction and a monochloro compound is obtained. Furthermore, in the case when a catalyst according to the present invention, or when the other catalysts are used or the first step reaction product is used, it turns out that the reactivity decreases and it takes a long time to complete the reaction, and a monochloro compound is obtained.

INDUSTRIAL APPLICABILITY

According to a method for preparing a phosphonitrilic acid ester of the present invention, it is possible to prepare a phosphonitrilic acid ester in which a monochloro compound content is very little and in extremely short time. Therefore, it becomes possible to shorten the reaction time and reduce the production cost and to prepare a phosphonitrilic acid ester with less costs. Thus, the present invention enables the industrial preparation of a useful phosphonitrilic acid ester with a low monochloro compound content, and improves anti-hydrolysis property and heat resistance of the phosphonitrilic acid ester itself. Furthermore, since decrease in the physical properties of a resin composition is suppressed, it can be expected that various derivatives of a phosphonitrilic acid ester oligomer or a phosphonitrilic acid ester polymer can be used in a wide range of applications such as a plastic and its additive agent, rubber, fertilizer, and medicine.

The invention claimed is:

1. A method for preparing a cyclic and/or linear phosphonitrilic acid ester represented by the formula (5)

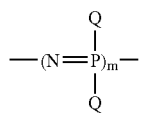

(5)

where Q represents an aryloxy group or an alkoxy group and m represents an integer of 3 or more, the method comprising:
reacting a cyclic and/or linear phosphonitrile dichloride with at least one compound selected from a phenolic compound and an alcohol compound in the presence of a reaction solvent,
wherein:
the cyclic and/or linear phosphonitrile dichloride is represented by the formula (1)

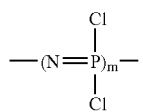

(1)

where m represents an integer of 3 or more,
the phenolic compound is represented by formula (2) or (3)

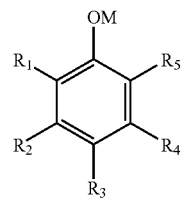

(2)

where M is a hydrogen atom or an alkaline metal, $R_1$ to $R_5$ are any of a hydrogen atom, an OM group, an aliphatic hydrocarbon group having 1 to 10 carbon atoms and an aromatic hydrocarbon group having 6 to 10 carbon atoms, and adjacent groups in $R_1$ to $R_5$ may form a ring

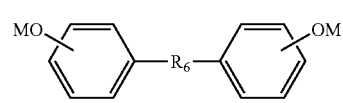

(3)

where M is a hydrogen atom or an alkaline metal, and $R_6$ is an aliphatic hydrocarbon group having 1 to 10 carbon atoms or an aromatic hydrocarbon group having 6 to 10 carbon atoms,
the alcohol compound is represented by the following general formula (4)

$R_7O\text{-}M$ (4)

where M is a hydrogen atom or an alkaline metal, and $R_7$ is an aliphatic hydrocarbon group having 1 to 10 carbon atoms,
(i) the reaction solvent is at least one solvent selected from aromatic hydrocarbons and halogenated hydrocarbons, and
(ii) the reaction is performed in the presence of a catalyst represented by the formula (6)

$(NH_4)_pA_qX_r$ (6)

where A is an element from one of groups IIA, IIIA, IVA, VA, VIA, VIIA, IB, IIB, IIIB, IVB, VB, VIB, VIIB and VIII in the long periodic table, X represents a halogen atom; p is an integer of 1 to 10, q is an integer of 1 to 10 and r is an integer of 1 to 35.

2. The method according to claim 1, wherein an alkaline metal salt of a phenolic compound and/or an alcohol compound is selected from at least one of a phenolic compound represented by the formula (2) or (3) and an alcohol compound represented by the formula (4).

3. The method according to according to claim 1, wherein the catalyst is a compound of the formula (6) in which A is Mg, Al, Cr, Co, Cu or Zn.

4. The method according to according to claim 1, wherein the reaction solvent used for preparing the phosphonitrilic acid ester is selected from at least one toluene, xylene, monochlorobenzene, dichlorobenzene and trichlorobenzene.

5. The method according to according to claim 1, wherein the amount of moisture in the reaction system is 0.2 mol or less per mol of phosphonitrile dichloride.

* * * * *

UNITED STATES PATENT AND TRADEMARK OFFICE
CERTIFICATE OF CORRECTION

| | | |
|---|---|---|
| PATENT NO. | : 7,514,520 B2 | Page 1 of 1 |
| APPLICATION NO. | : 10/557722 | |
| DATED | : April 7, 2009 | |
| INVENTOR(S) | : Kotaro Kuwata et al. | |

It is certified that error appears in the above-identified patent and that said Letters Patent is hereby corrected as shown below:

Column 40, Line 52, before "claim" delete "according to".

Column 40, Line 55, before "claim" delete "according to".

Column 40, Line 59, before "claim" delete "according to".

Signed and Sealed this

Sixteenth Day of June, 2009

JOHN DOLL
*Acting Director of the United States Patent and Trademark Office*